United States Patent
Shenk et al.

(10) Patent No.: US 8,548,764 B1
(45) Date of Patent: *Oct. 1, 2013

(54) METHOD AND SYSTEM FOR INCREASING OPTICAL INSTRUMENT CALIBRATION AND PREDICTION ACCURACY WITHIN AND ACROSS DIFFERENT OPTICAL INSTRUMENT PLATFORMS

(75) Inventors: John S. Shenk, Columbia, MD (US); John W. Shenk, Columbia, MD (US); Bill Brown, Columbia, MD (US); Paolo Berzaghi, Columbia, MD (US)

(73) Assignee: Westco Scientific Instruments, Inc., Brookfield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/339,493

(22) Filed: Dec. 29, 2011

Related U.S. Application Data

(63) Continuation of application No. 12/357,830, filed on Jan. 22, 2009, now Pat. No. 8,108,170.

(60) Provisional application No. 61/011,853, filed on Jan. 22, 2008.

(51) Int. Cl.
*G01D 18/00* (2006.01)
*G01R 35/00* (2006.01)

(52) U.S. Cl.
USPC .................. 702/85; 356/319; 702/179; 703/2

(58) Field of Classification Search
USPC ....... 702/28, 30, 85, 108, 127, 179; 356/308, 356/319; 703/2
See application file for complete search history.

(56) References Cited

U.S. PATENT DOCUMENTS

| | | | |
|---|---|---|---|
| 4,866,644 A | 9/1989 | Shenk et al. | |
| 4,969,739 A | 11/1990 | McGee | |
| 5,459,677 A | 10/1995 | Kowalski et al. | |
| 6,560,546 B1 | 5/2003 | Shenk et al. | |
| 6,615,151 B1 | 9/2003 | Scecina et al. | |
| 7,038,744 B2 | 5/2006 | Kuzuhara et al. | |
| 7,127,372 B2 | 10/2006 | Boysworth | |
| 8,108,170 B1 * | 1/2012 | Shenk et al. | 702/85 |

OTHER PUBLICATIONS

Donald A. Burns, et al., Handbook of Near-Infrared Analysis, 808 pgs., Published by CRC Press, 2007, (Abstract 1-pg).

* cited by examiner

*Primary Examiner* — John H Le
(74) *Attorney, Agent, or Firm* — Thomas | Horstemeyer, LLP

(57) ABSTRACT

A method and system for increasing optical instrument calibration and prediction accuracy within and across different optical instrument platforms can include two main sub-methods or routines. The first routine can include one for correcting differences among optical instruments of different model types regardless of the manufacturer and correcting differences among optical instruments of the same model type. The second main routine or sub-method can include one for analyzing new samples of a product over time and maintaining prediction accuracy as compared to a reference method over time. The first routine can include a "TRANS" procedure, a "MIN" procedure, and checkcell tests. The second main routine provides techniques on how a product database can be cleaned, condensed, and expanded automatically as it is used by one or more different optical instruments.

20 Claims, 14 Drawing Sheets

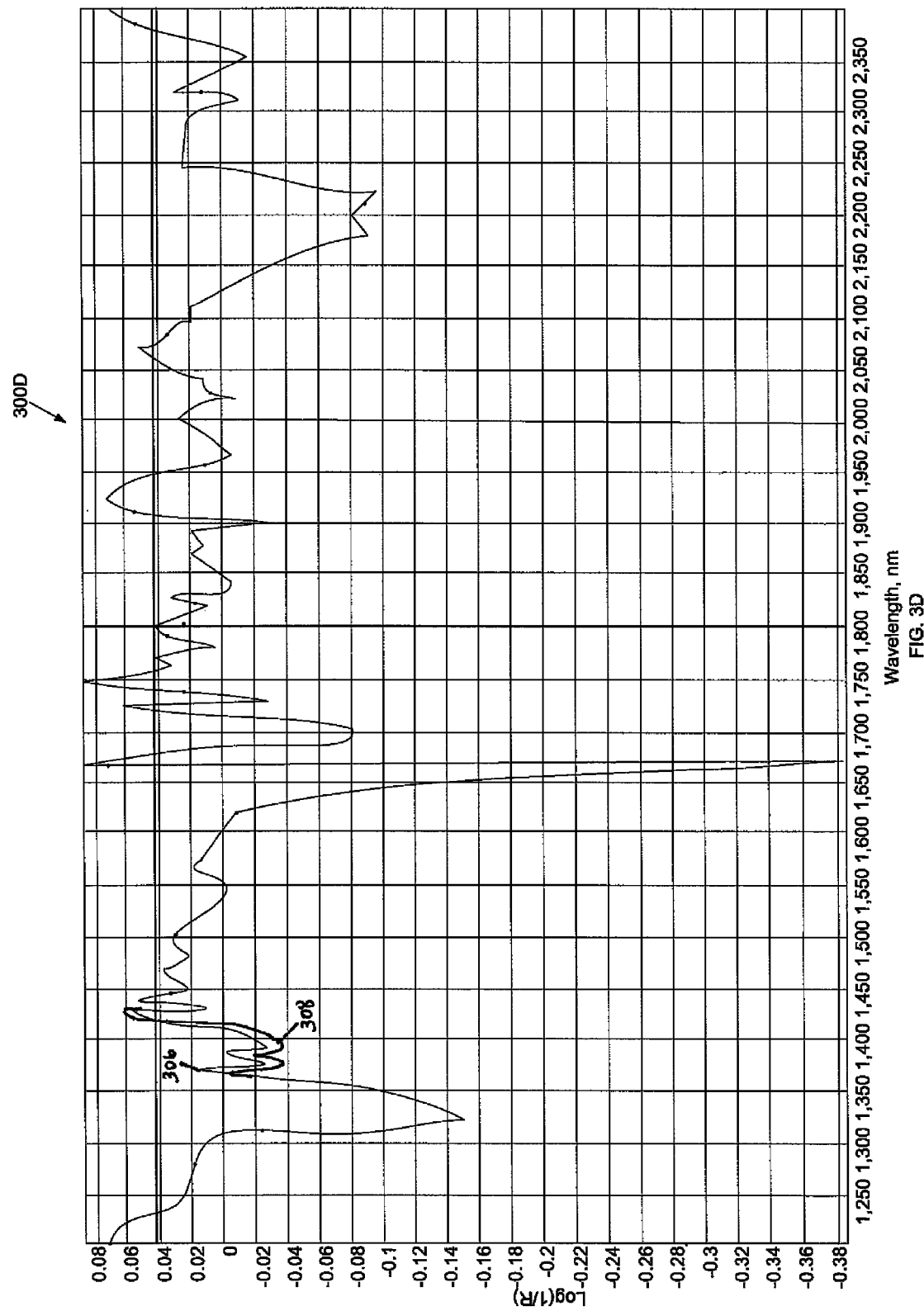

METHOD AND SYSTEM FOR INCREASING OPTICAL INSTRUMENT CALIBRATION AND PREDICTION ACCURACY WITHIN AND ACROSS DIFFERENT OPTICAL INSTRUMENT PLATFORMS

STATEMENT REGARDING RELATED APPLICATIONS

The present application claims priority to Non-provisional patent application entitled, "METHOD AND SYSTEM FOR INCREASING OPTICAL INSTRUMENT CALIBRATION AND PREDICTION ACCURACY WITHIN AND ACROSS DIFFERENT OPTICAL INSTRUMENT PLATFORMS," filed an Jan. 22, 2009 and assigned U.S. application Ser. No. 12/357,830; the entire contents of which are incorporated by reference.

FIELD OF THE INVENTION

The invention relates generally to the operation of spectrographic instruments, and more particularly to a simple and improved system for assuring the accuracy of spectrographic instruments and their calibration based on results obtained from such instruments, regardless of the instrument's manufacturer.

BACKGROUND OF THE INVENTION

Spectrographic instruments are used to provide accurate analysis of materials. The most common of these instruments is the spectrophometer. Spectrophometers measure intensity of light absorption and/or reflectance that occurs when a sample is exposed to electromagnetic radiation. Typically, spectrophotometers measure the absorption and/or reflectance of visible, near-ultraviolet, and near-infrared light. The main components of a spectrophometer include an electromagnetic radiation source, a chamber for holding a sample, and an electromagnetic radiation detector.

The function of a standard spectrophometer can be briefly described as follows: (1) electromagnetic radiation at a specific wavelength is directed toward the sample; (2) the sample absorbs a specific amount or radiation; (3) the detector detects how much radiation the sample absorbed at the specific wavelength; (4) the detector converts the amount of radiation absorbed into a number; (5) the number is plotted on a graph and the process then repeats for a different wavelength until the full selected spectrum of electromagnetic radiation has been analyzed.

Spectrographic instruments can be used to determine measurable characteristics of the materials under analysis. For example, concentrations of constituents in the materials or alternatively, physical characteristics of the materials may be measured. In agriculture, spectrographic instruments are used to determine the oil, protein, and moisture content of grain, the fat content of meat, the fat, protein and lactose content of mile, and urea content of milk. Spectrographic instruments are also used to analyze blood samples, pharmaceuticals and synthetic resins.

It is well known when a number of spectrographic instruments measure the same sample, each instrument will generally produce an instrument specific signal if no actions are taken to ensure that the signals produced by the instruments are identical for a particular sample. The reasons for this include variation in the components for each instrument, variation in the instruments' age, repairs to a particular instrument, and fluctuations in the operating environment. It is equally well known that it is desirable to be able to manufacture spectrographic instruments which generate the same spectra absorption results when analyzing the same sample. There are some techniques in the field designed to correct for these problems.

Another dimension to the problems described above stems from the use of different spectrographic instruments from different manufactures. Large companies that make extensive use of spectrographic instruments often use instruments made by a variety of manufacturers. Price fluctuation is one reason for this. Another is that certain manufactures produce instruments for particular tasks. For example, manufacturer A produces an instrument specifically designed for moisture content of grain while manufacturer B produces instruments tailored for measuring the urea content of milk. A large agricultural firm would require the use of both instruments. But in order to calibrate both, the company would need to use the particular calibration system offered by each manufacturer to calibrate the respective machines. A plurality of calibration systems is expensive and makes it inconvenient to share information across instrument platforms.

Moreover, known techniques for multi-instrument calibration lack accuracy and ease of use. Some methods require measurements to be taken on the target instruments for a plurality of transfer samples. The transfer samples must contain known values for the property under consideration. Accordingly, if the operator of the target machine desired to analyze a new property in a sample, the operator would have to obtain transfer samples for the property in question that have been scanned in a reference instrument and then scanned in the target instrument before the operator can scan the target sample. This time-consuming procedure is not well suited for the modern production facility where efficiency is a top priority.

Other problems in the art include those associated with prediction methods for spectrographic instruments. The goal a prediction method when it is employed for a spectrographic instrument is to determine unknown properties of a sample. In other words, prediction methods allow for quantitative analysis. Whether the operator is looking for the fat content of a particular hybrid of wheat, or the octane level of gasoline, the operator can scan the sample, plug the scan results into the prediction method, and calculate a value for the property under analysis. A basic prediction method involves the use of a spectra library, mathematics, and equations that are applied to the product (spectra) library to generate a value for the unknown property of the sample.

The problem for an operator who is trying to improve his prediction method is the inability to easily expand the spectra library. Currently, spectra library expansion occurs only through persons who are highly skilled in the art of spectroscopy. In addition to the inability to easily expand the library, the continuous expansion of a spectra library may actually hurt the accuracy of predictions if the library becomes too large or redundant for the prediction method to properly sort through.

Therefore, there is a need in the art for a calibration system capable of calibrating spectrographic instruments regardless of manufacturer and regardless of the particular manufacturer's operation method and calibration method. In addition, there is also a need in the art for a system that can combine the multi-instrument calibration method discussed above with a method for accurately predicting properties about an unknown sample scanned in a spectrographic instrument.

A further need exists in the art for an easily-updatable spectra database and a prediction method that can access the database, as well as ensure that the accuracy of its predictions will not decline as the database expands. There is a need in the art for a system and method that combines both a calibration method and a prediction method that is easy to use for a spectrographic instrument operator. A need also exists in the art for a spectrographic system which has a high level of accuracy—both in its ability to produce consistent readings over the life of a particular spectrographic instrument as well as the ability of the spectrographic instrument to predict unknown properties of a sample.

SUMMARY OF THE INVENTION

A method and system for increasing optical instrument calibration and prediction accuracy within and across different optical instrument platforms can comprise two main sub-methods or routines. This first routine can be referred to generally as "Optical Instrument Spectral Accuracy." The first routine can include one for correcting differences among optical instruments of different model types regardless of the manufacturer and correcting differences among optical instruments of the same model type. The second main routine or sub-method can include one for analyzing new samples of a product over time and maintaining prediction accuracy as compared to a reference method over time. This second main routine 110 can be referred to generally as "Optical Instrument Prediction Accuracy."

This first routine can include a "TRANS" procedure, a "MIN" procedure, and checkcell tests. The "TRANS" procedure generates a TRANS file that functions to make the optical instrument model being tested to be like ("transforms" the instrument to be like) other optical instruments of a different model.

According to the TRANS procedure, sealed product standards can be scanned by a master instrument (which is one of the same optical instrument models that generates a product database). The sealed product standards are also scanned by the optical instrument under consideration (which can be a different model relative to the master instrument). The scans between the master instrument and the optical instrument under consideration are compared mathematically to produce the TRANS file.

The MIN procedure of the first main routine generates a MIN file. The MIN file "minimizes" differences among optical instruments of the same model. This MIN procedure is accomplished by scanning at least one sealed product standard on about five to ten optical instruments of the same optical instrument model being evaluated. The MIN file produced by the MIN procedure, is also known as a Repeatability or REP file, and is produced by techniques known to one of ordinary skill in the art. A MIN or REP file usually contains spectra of one or more sealed standard products scanned under different conditions.

The three tests of the first routine require scans of a checkcell: a wavelength accuracy test, a photometric accuracy test, and a prediction repeatability test. A checkcell is a container that confines a material which has consistent optical properties over the life of an optical instrument and which can determine optical instrument variations over time. The checkcell used with an optical instrument should be the same one which is used over the life of the optical instrument.

The second main routine, as noted above, analyzes new samples of a product over time and maintaining prediction accuracy as compared to a reference method over time. This second main routine can be referred to generally as "Optical Instrument Prediction Accuracy." According to this second main routine, a product database can be cleaned, condensed, and expanded. Prior to cleaning, the constituents of a product database are separated. Constituents are generally the chemical properties of a product. For example, a product database for wheat may have constituents of protein, moisture, and fiber content.

After separation of the database into constituents, the product database can be cleaned of outlier samples by using Neighborhood H (NH), Global H (GH), and the T values which are generated by applying Partial Least Squares (PLS) to each constituent database. After cleaning the database, the average NH is calculated for each constituent database. Then Condensing is performed by changing the size of the average NH value by a constant or percentage (%) (such as by 10, 20, or 30% etc). This then creates a threshold. All of the sample values inside these expanded neighborhoods are then averaged (both spectra and reference values) giving the reduced number of samples in the constituent database (from the previous cleaning). Then the PLS method, which has a regression equation, is applied to the values of the increased neighborhood for calculating new NH and GH values.

Each condensed constituent database is then recalculated with PLS and the last constituent equation is made along with its GH and NH values. This means that three PLS regression equations have been developed for each constituent database: The first is made with all clean samples of each cleaned constituent database; the second with the increases in NH size for each constituent database; and the last (third) after each constituent database is condensed.

After the product database is cleaned and condensed, it can be used by optical instruments to predict properties of samples being scanned. If any of the samples being scanned cannot be found in the product database, the optical instrument through its software can flag these unmatched samples and place them in an expansion file. The optical instrument can prompt the operator to provide reference values for the unmatched samples and put these reference values in the expansion file.

A computer server can receive the expansion files and automatically separates the product database again into constituents. The separated database can then be cleaned, compressed, and restructured to include the samples which were previously not found in the product database. This expansion of the product database can be performed as often as needed for a given situation. With this system and method, a historical record of the performance of a particular optical instrument is made. Further, with this system and method, management of numerous optical instruments spread out over large geographies can be accomplished from a central location.

BRIEF DESCRIPTION OF THE DRAWINGS

FIG. 3D illustrates plots or graphs of spectra generated by at least two optical instruments of the same model measuring the same checkcell and which have been treated mathematically according to one exemplary embodiment of the invention.

DETAILED DESCRIPTION OF EXEMPLARY EMBODIMENTS OF THE INVENTION

Figure 1A:
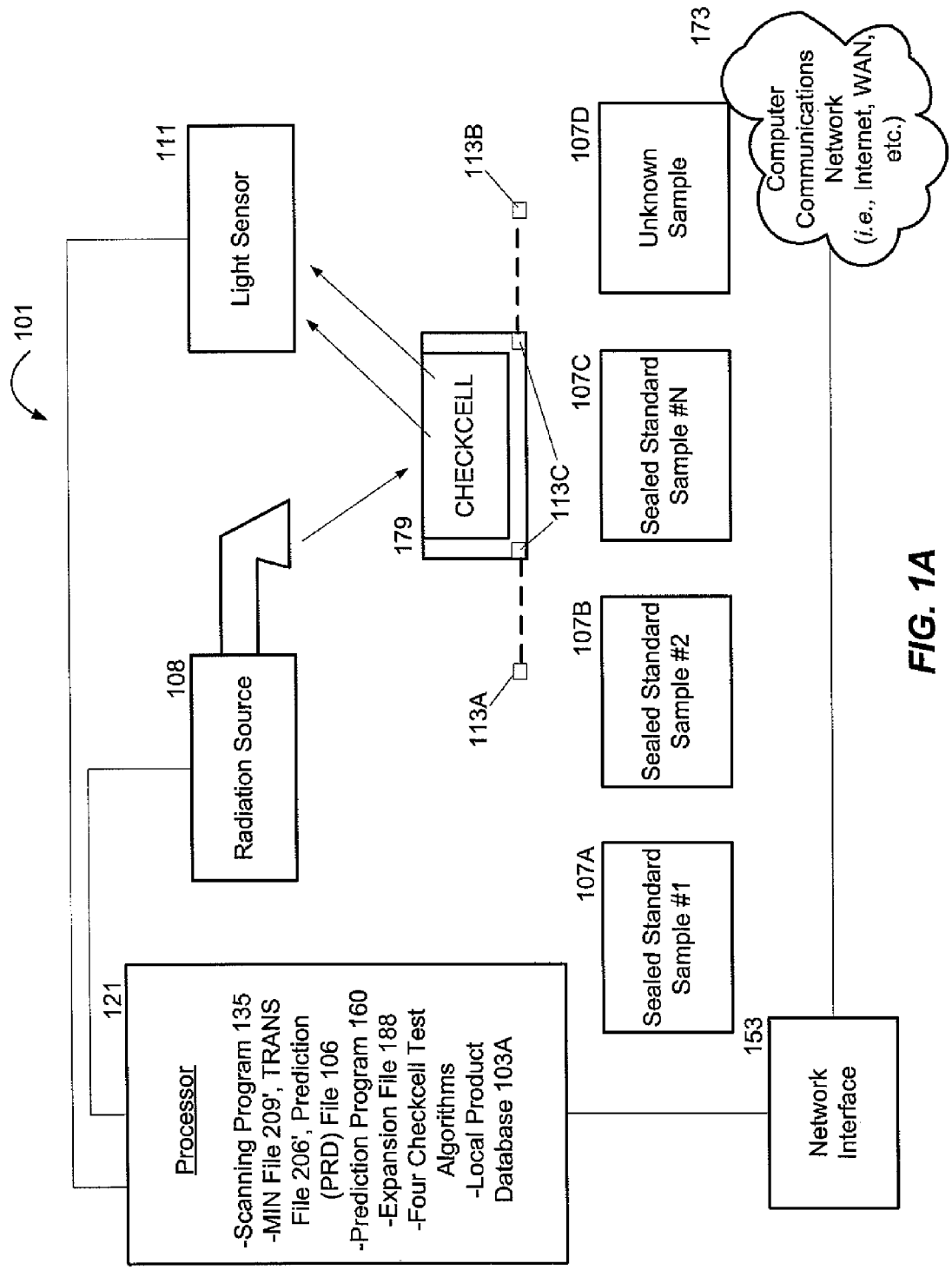
FIG. 1A is a functional block diagram illustrating a client optical instrument coupled to a computer network 173 according to one exemplary embodiment of the invention.

Referring now to the drawings, in which like numerals represent like elements throughout the several Figures, aspects of the present invention and the illustrative operating environment will be described. FIG. 1A is a functional block diagram illustrating a client optical instrument 101 coupled to a computer network 173 according to one exemplary embodiment of the invention. The optical instrument 101 can comprise a radiation source 108, a light sensor 111, and a processor 121. The radiation source 108 can comprise a laser for emitting light, such as near infrared (NIR) light according to an exemplary embodiment. However, other radiation sources are not beyond the invention. The laser of the radiation source 108 can produce light in the wavelength region between about 1100 nanometers and about 2500 nanometers.

The light sensor 111 can comprise a photodetector for receiving and detecting the light generated by the radiation source 108 and which is reflected off an object, such as a checkcell 179, a sealed standard sample 107A-C, or an unknown sample 107D. The light sensor 111 converts the received light from the radiation source 108 into electrical signals which are fed into the processor 121 of the optical instrument 101.

The processor 121 can comprise a central processing unit (CPU) of a general purpose computer as will be described in further detail below in connection with FIG. 1D. The processor 121 can execute or run various software programs as well as storing various files locally. With various software, the processor 121 can help predict the physical properties of an object being scanned based on how light produced by the radiation source 108 is absorbed and/or reflected by an object being scanned.

Some of the software which is executed by the processor 121, can include, but is not limited to, a scanning program 135, a prediction program 160, and three checkcell test algorithms 212, 215, 218 as described below in connection with FIG. 2. The processor 121 can also access, update, and retrieve various files stored locally such as a MIN file 209, a TRANS file 206, a prediction (PRD) file 106, and a local product database 103A.

Figure 1B:
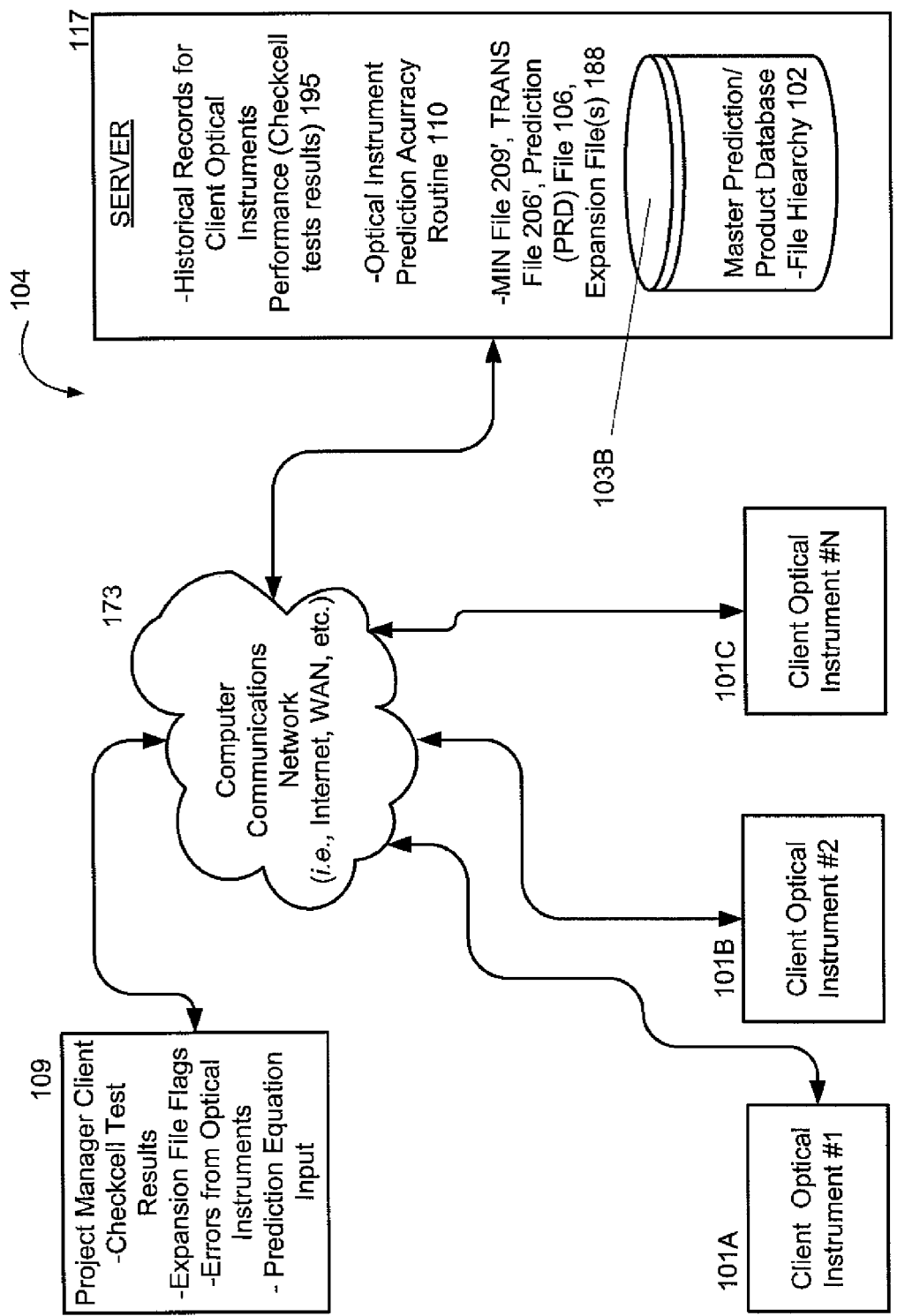
FIG. 1B illustrates a system 104 for increasing optical instrument calibration and prediction accuracy within and across different optical instrument platforms according to one exemplary embodiment of the invention.

While the local product database 103A has been illustrated in FIG. 1B as part of the computer server 117, one of ordinary skill in the art recognizes that the database 103A could be physically separate from the computer server 117, such as its own relational database management system. If separate from the computer server 117, the relational database could comprise a structured query language, such as MySQL as a general example.

The scanning program 135 can control the radiation source 108 and light sensor 111. It can help the optical instrument 101 produce the scans with the radiation source 108 that are further processed and assessed by the prediction program 160. The prediction program 160 can analyze the scans and compare them to the local product database 103A. The local product database 103A can comprise spectra data and reference values for a product, such as wheat. Other products which can be scanned by the optical instrument 101 are not beyond the invention. Other products can be from any number of classes of materials, such as biological (plants, animal tissue, etc.), synthetic (man-made) materials (resins, pharmaceuticals, etc.), or naturally occurring materials (metals, soil, etc.). Further, while the scanning program 135 and the prediction program 160 have been described as separate program modules, one of ordinary skill in the art recognizes that these programs could be formed and executed as a single program without departing from the scope of the invention.

Further details of checkcell test algorithms 212, 215, and 218, as well as the MIN file 209 and TRANS file 206 will be described below in connection with FIG. 2 below. Further details of the prediction (PRD) file 106 and a local product database 103A will be referenced throughout the discussion of FIGS. 2 and 4.

The processor 121 is coupled to a network interface 153 which is in turn coupled to a computer communications network 173. The network interface 153 can comprise hardware and software which allows the processor 121 to communicate over the communications network 173. The communications network 173 can include local area networks (LANs,) wide area networks (WAN), the Internet. The network interface 153 can be for a wired network or a wireless network.

The checkcell 179 is preferably made with a material or set of materials which have consistent optical properties over time. The material or materials of the checkcell 179 are sealed in a container which can reduce or eliminate environmental noise that can be produced by such elements like moisture, dirt, dust, etc. According to one exemplary embodiment, the material used for scanning in the checkcell 179 is made from acetyl. Acetyl can produce a spectrum which has relatively constant amplitudes of intensity across the wavelengths forming its spectrum. Acetyl has consistent optical properties over time on the order of several years and decades. However, other materials for the checkcell 179 that may have relatively constant amplitudes of intensity across various wavelengths over long periods of time are not beyond the invention.

According to one exemplary embodiment, the container for the checkcell 179 can comprise a metal cylinder with a hollow interior made from stainless steel. The material of the checkcell 179 which will be scanned, such as acetyl, can be positioned within the hollow interior of the container. Other shapes and materials for the container are not beyond the scope of the invention.

The consistent optical properties of the checkcell 179 can be important because, according to one exemplary embodiment of the invention, each checkcell 179 is assigned to a specific optical instrument 101 at the factory or when the optical instrument 101 is first used in the field. In other words, each optical instrument 101 will use the same checkcell 179 over the course of the instrument's operating life. In this way, the physical properties of the checkcell 179 are controlled and should remain consistent. This means that the checkcell 179 should not constitute a variable when the accuracy of the scans produced by the optical instrument 101 is being assessed, as described in further detail below.

In addition to the chemical properties of the checkcell being controlled and not variable over time, the actual physical orientation of the checkcell 179 when it is scanned should also remain constant over the life of the optical instrument 101. In order to achieve consistent physical placement of the checkcell 179, alignment mechanisms 113A, 113B, 113C may be provided which can help an operator to orient the checkcell 179 within the optical instrument 101 over the life of the optical instrument 101.

The alignment mechanisms 113A, 113B positioned on the optical instrument 101 can include physical objects such as projections that can be used in conjunction with alignment mechanisms 113C positioned on the checkcell 179. The alignment mechanisms on the checkcell 113C can comprise indentations, projections, or markings that can be used to orient the checkcell 179 properly relative to the on-scanner alignment mechanisms 113A, 113B. Other alignment mechanisms 113 not illustrated but function to allow repeatable and consistent orientation of a checkcell 179 and/or samples within the optical instrument are not beyond the scope of the invention.

In some exemplary embodiments, alignment mechanisms 113 may not be needed. For example, some optical instruments 101 provide a platform which rotates samples 107D while they are scanned by the optical instrument 101. In such optical instruments 101 with rotating platforms, alignment mechanisms 113 may not be needed since the orientation of the checkcell 179 within the optical instrument 101 is not variable.

The sealed standard samples 107, like the checkcell 179 described above; should have optical properties which are consistent over long periods of time such as the order of several years and more specifically, for the operating life of a particular optical instrument 101. The sealed standard samples 107 should be resistant to environmental elements such as dirt, dust, temperature, light, moisture, etc. Sealed standard samples 107 should be selected so that the samples 107 represent a broad spectrum of all products that will likely scanned by a particular optical instrument 101.

For example, if the optical instrument 101 will be used for measuring agricultural products, then it has been discovered by the inventors that the following five sealed standard samples 107 provide a sufficient baseline spectra to help calibrate an optical instrument over a broad spectral range to address many types of agricultural products: (a) forage, (b) wheat, (c) flour, (d) concentrate, and (e) fish meal. However, other standard samples for agricultural products are not beyond the invention. And other products, besides agricultural products, are also within the scope of the invention, such as naturally occurring substances like soil, dirt, metals as well as synthetic (man-made substances) like polymers, and biological materials like blood, urine, plasma, etc.

Referring now to FIG. 1B, a system 104 for increasing optical instrument calibration and prediction accuracy within and across different optical instrument platforms is illustrated. A server computer 117 can be coupled to a computer communications network 173 such as a local area network (LAN), wide area network (WAN), or the Internet. A plurality of client optical instruments 101A, 101B, and 101C, like the one illustrated in FIG. 1, may also be coupled to the computer communications network 173 so that the client optical instruments 101 can send and receive data from the computer server 117 and a client project manager 109.

The computer server 117 can retrieve and store various information about the optical instruments 101. The computer server 117 can access historical records 195 that address each client optical instrument's performance over time. The computer server 117 can also maintain and update a master prediction/product database 103B which can have a structured hierarchy 102, as will be discussed below in connection with FIG. 1C. The computer server 117 can also execute or perform various programs such as an optical instrument prediction accuracy routine 110 which will be described in further detail below with respect to FIG. 1E. Other programs executed by the computer server 117 are not beyond the invention.

The computer server 117 can also access and maintain several files which may be used by the client optical instruments 101 during scanning of products. Such files can include, but is not limited to, a MIN file 209, a TRANS file 206, a prediction (PRD) file 106, and expansion files 188.

As noted previously, the computer communications network 173 as well as the links between the client optical instruments 101 and the computer communications network 173 may be wired or wireless. That is, traditional computer cables can couple the optical instruments 101 to the computer communications network 173. Alternatively, wireless links such as those which use radio frequency waves may also be employed to couple the optical instruments 101 to the computer communications network 173 without departing from the invention.

The project manager client 109 can comprise a computer 120, similar to the one illustrated in FIG. 1D and will be described in detail below. The project manager client 109 can receive various messages from the computer server 117 such as, but not limited to, results of the checkcell tests performed on the optical instruments 101, expansion file flags of a routine 612 as will be described below in FIG. 6; and error messages generated by any of the optical instruments 101. The project manager client 109 can also receive input comprising prediction equations that an operator of the project manager client 109 may select for a particular optical instrument 101. The operator of the project manager client 109 is generally responsible for trouble shooting any of the optical instruments 101 which are coupled to the computer communications network 173 and computer server 117.

Figure 1C:
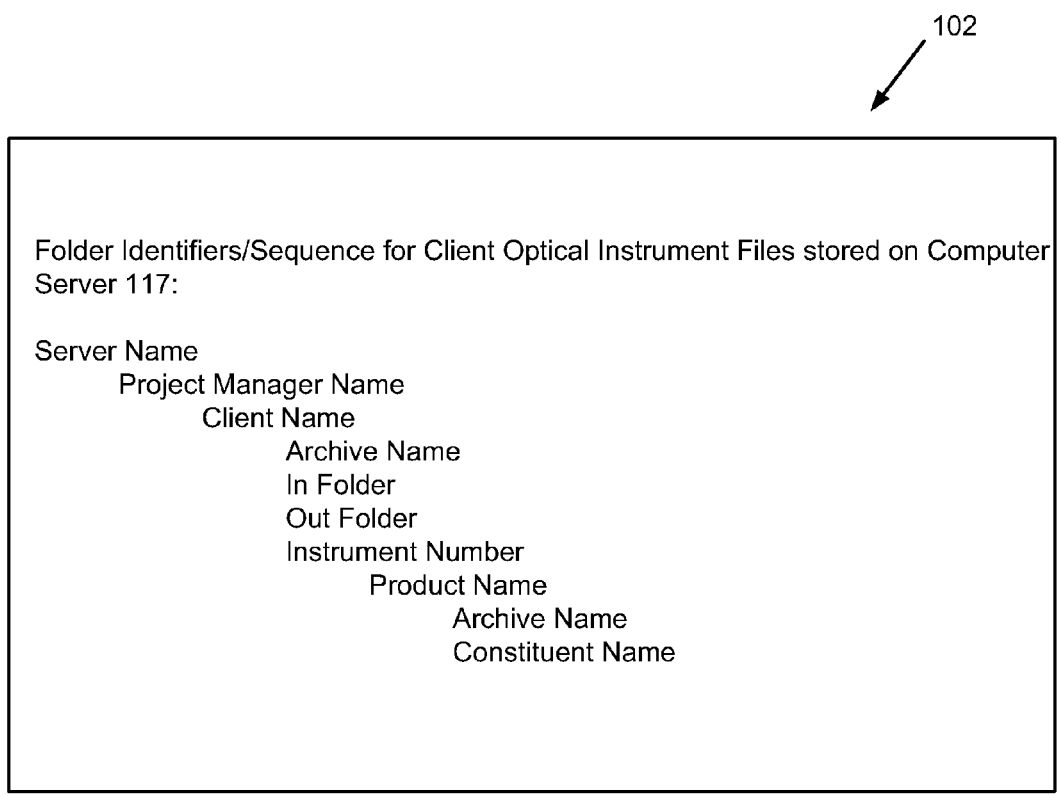
FIG. 1C illustrates an exemplary framework or hierarchy for computer files that can be managed by the computer server illustrated in FIG. 1B according to one exemplary embodiment of the invention.

Referring now to FIG. 1C, this Figure illustrates an exemplary framework or hierarchy 102 for files that can be managed by the computer server 117 in FIG. 1B. This computer server 117 can support or serve a plurality of optical instruments 101 that can provide data which is stored in the files. The hierarchy 102 can include, but is not limited to, a name assigned to the server 117; a name of a project manager (a person); a client name, Archive name; an In Folder; an Out Folder; an Instrument Model Number; a Product Name; Archive name; and Constituent Name.

The client name can comprise an identifier for a legal entity, such as a corporate name. The product name usually corresponds to the products which are scanned with the optical instrument 101. For example, a product like wheat could be a product that is scanned by an optical instrument. A constituent name usually includes a name for a chemical property of the product that can produce a spectrum which is detectable by an optical instrument. In the example product of wheat, constituents can include, but are not limited to, protein, moisture, and fiber. The "In Folder" is the section of the file hierarchy 102 which can contain data uploaded to the computer server 117 by the client optical instrument 101. The "Out Folder" is the section of the file hierarchy 102 which can contain data that may be downloaded from the computer server 117 to client optical instrument 101.

One of ordinary skill in the art recognizes that other frameworks or hierarchies 102 could be adopted without departing from the scope of the invention. For example, other hierarchies could include a fewer number or a greater number of files or fields. As a further example, according to another exemplary embodiment, the hierarchy 102 could include a name or employee number for an operator of an optical instrument 101.

Figure 1D:
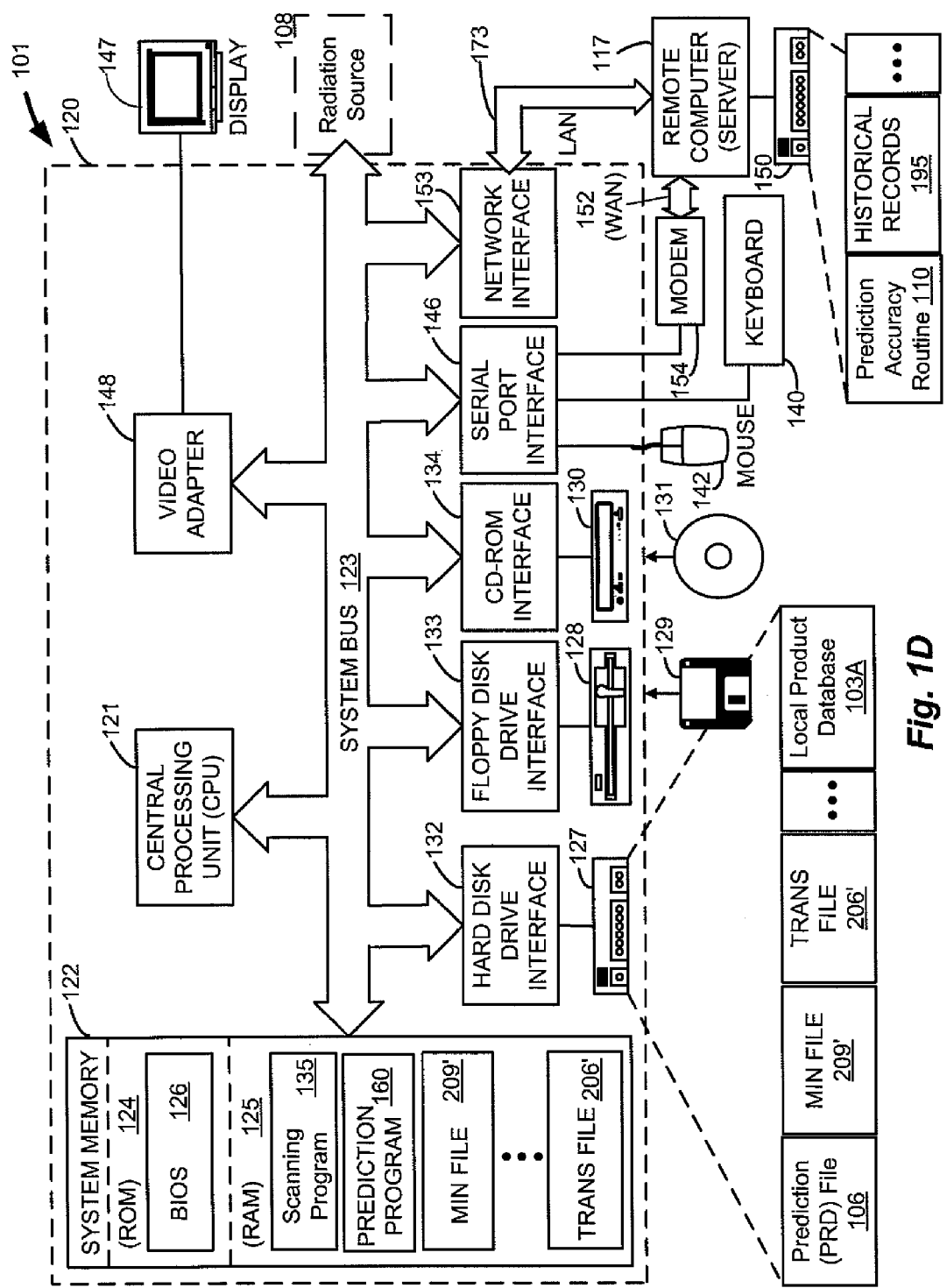
FIG. 1D is a functional block diagram of a computer that is part of the optical instrument of FIG. 1A and that can be used in the system for increasing optical instrument calibration and prediction accuracy within and across different optical instrument platforms according to one exemplary embodiment of the invention.

Referring now to FIG. 1D, this figure is a functional block diagram of a computer 120 that is part of the optical instrument 101 of FIG. 1A and that can be used in the system 104 for increasing optical instrument calibration and prediction accuracy within and across different optical instrument platforms. The exemplary operating environment for the system 104 includes a general-purpose computing device in the form of a conventional computer 120. Generally, the computer 120 includes a processing unit 121, a system memory 122, and a system bus 123 that couples various system components including the system memory 122 to the processing unit 121.

The system bus 123 may be any of several types of bus structures including a memory bus or memory controller, a peripheral bus, and a local bus using any of a variety of bus architectures. The system memory includes a read-only memory (ROM) 124 and a random access memory (RAM) 125. A basic input/output system (BIOS) 126, containing the basic routines that help to transfer information between elements within computer 120, such as during start-up, is stored in ROM 124.

Computer 1120 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD-ROM or other optical media. Hard disk drive 127, magnetic disk drive 128, and optical disk drive 130 are connected to system bus 123 by a hard disk drive interface 132, a magnetic disk drive interface 133, and an optical disk drive interface 134, respectively.

Although the exemplary environment described herein employs hard disk 127, removable magnetic disk 129, and removable optical disk 131, it should be appreciated by those skilled in the art that other types of computer readable media which can store data that is accessible by a computer, such as magnetic cassettes, flash memory cards, digital video disks, Bernoulli cartridges, RAMs, ROMs, and the like, may also be used in the exemplary operating environment. The drives and their associated computer readable media provide nonvolatile storage of computer-executable instructions, data structures, program modules, and other data for computer 120.

A number of program modules may be stored on hard disk 127, magnetic disk 129, optical disk 131, ROM 124, or RAM 125, including a scanning program 135, and a prediction program 160. Files such as a MIN file 209 and TRANS file 206 can be stored and accessed in RAM 125. Program modules include routines, sub-routines, programs, objects, components, data structures, etc., which perform particular tasks or implement particular abstract data types. Aspects of the present invention may be implemented in the form of the prediction program 160 communicating with a remote computer server 117.

A user may enter commands and information into computer 120 through input devices, such as a keyboard 140 and a pointing device 142. Pointing devices may include a mouse, a trackball, and an electronic pen that can be used in conjunction with an electronic tablet. Other input devices (not shown) may include a microphone, joystick, game pad, satellite dish, scanner, or the like. These and other input devices are often connected to processing unit 122 through a serial port interface 146 that is coupled to the system bus 123, but may be connected by other interfaces, such as a parallel port, game port, a universal serial bus (USB), or the like. A display device 147 may also be connected to system bus 123 via an interface, such as a video adapter 148. In addition to the monitor, computers typically include other peripheral output devices (not shown), such as speakers and printers.

The computer 120 may operate in a networked environment using logical connections to one or more remote computers 100E. Remote computer 100E may be another personal computer, a server, a client, a router, a network PC, a peer device, or other common network node. In one preferred and exemplary embodiment, the remote computer 117 comprises the computer server 117, like the one described above in FIG. 1B. While the remote computer 117 typically includes many or all of the elements described above relative to the computer 120, only a memory storage device 150 has been illustrated in FIG. 1D. The logical connections depicted FIG. 1D include a local area network (LAN) 173 and a wide area network (WAN) 152. Such networking environments are commonplace in offices, enterprise-wide computer networks, intranets, and the Internet.

When used in a LAN networking environment, the computer 120 is often connected to the local area network 173 through a network interface or adapter 153. When used in a WAN networking environment, the computer 120 typically includes a modem 154 or other means for establishing communications over WAN 173, such as the Internet. Modem 154, which may be internal or external, is connected to system bus 123 via serial port interface 146. In a networked environment, program modules depicted relative to computer 120, or portions thereof, may be stored in the remote memory storage device 150. It will be appreciated that the network connections shown are exemplary and other means of establishing a communications link between the computers may be used.

Moreover, those skilled in the art will appreciate that the present invention may be implemented in other computer system configurations, including hand-held devices, multiprocessor systems, microprocessor based or programmable consumer electronics, network person computers, minicomputers, mainframe computers, and the like. The invention may also be practiced in distributed computing environments, where tasks are performed by remote processing devices that are linked through a communications network. In a distributed computing environment, program modules may be located in both local and remote memory storage devices.

Figure 1E:
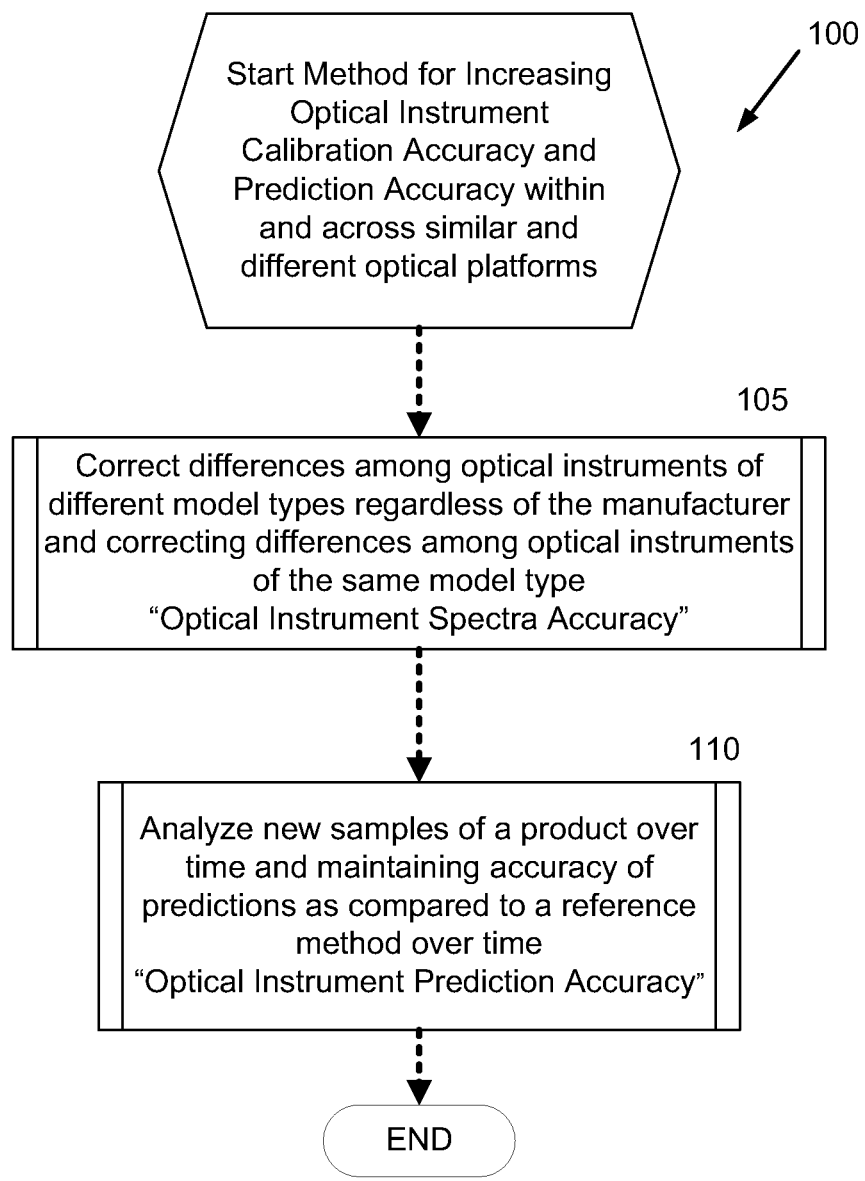
FIG. 1E illustrates an exemplary logic flow chart highlighting two main routines of a method for increasing optical instrument calibration and prediction accuracy within and across different optical instrument platforms according to one exemplary embodiment of the invention.

Method for Increasing Optical Instrument Calibration Accuracy and Prediction Accuracy Within and Across Similar and Different Optical Platforms Referring now to FIG. 1E, this Figure illustrates an exemplary logic flow chart highlighting two main routines 105, 110 of a method 100 for increasing optical instrument calibration and prediction accuracy within and across different optical instrument platforms. One of ordinary skill in the art will appreciate that the functions and operations of flowchart illustrated in FIG. 1E and flow charts of the remaining figures can be executed with firmware code executing on a microcontroller, microprocessor, a DSP, or state machines implemented in application specific or programmable logic, or other numerous forms without departing from the spirit and scope of the invention.

In other words, these steps illustrated in FIG. 1E and other logic flow diagrams of this disclosure maybe provided as a computer program which may include a machine-readable medium having stored there on instructions which maybe used to program a computer (or other electronic devises) to perform a process according to the invention. The machine-readable medium may include, but is not limited, floppy diskette, optical disk, CD-ROM, magneto-optical disks, ROMs, RAMs, EEPROMs, EEPROMs, magneto-optical cards, flash memory, or other type of medias/machine-readable mediums suitable for storing electronic instructions.

Further, Certain steps in the processes or process flow described in all of the logic flow diagrams refer to in this disclosure must naturally precede others for the invention to function as described. However, the invention is not limited to the order of the steps described if such order or sequence does not alter the functionality of the present invention. That is, it is recognized that some steps may perform before, after, or parallel other steps without departing from the scope and spirit of the invention. Further, one of ordinary skill in programming would be able to write such a computer program or identify appropriate hardware at circuits to implement the disclosed invention without difficulty based on the flow charts and associated description in the application text, for example.

Therefore, disclosure of a particular set of program code instructions or detailed hardware devices is not considered necessary for an adequate understanding of how to make and use the invention. The inventive functionality of the claimed computer implemented processes will be explained in more detail in the following description and in conjunction with the remaining figures illustrating other process flows.

Referring back again to FIG. 1E, the first routine 105 and second routine 110 are joined by dashed arrowed lines to indicate that the order or sequence of these two routines could be changed without changing the scope of the invention. The dashed arrowed lines also indicate that the overall process can stop after either of these two routines.

The first main routine 105 can include one for correcting differences among optical instruments 101 of different model types regardless of the manufacturer and correcting differences among optical instruments 101 of the same model type. This first routine 105 can be referred to generally as "Optical Instrument Spectral Accuracy." Further details of the first routine 105 will be described below in connection with FIG. 2.

The second main routine or sub-method 110 can include one for analyzing new samples of a product over time and maintaining prediction accuracy as compared to a reference method over time. This second main routine 110 can be referred to generally as "Optical Instrument Prediction Accuracy." A reference method generally refers to a method which is validated such as traditional chemical analysis. Meanwhile, using spectrographic optical instruments 101 to assess physical properties of products are not validated methods and do not yield true measurements of the physical properties being measured. Further details for of the second routine or sub-method 105 will be described below in connection with FIG. 2.

Figure 2:
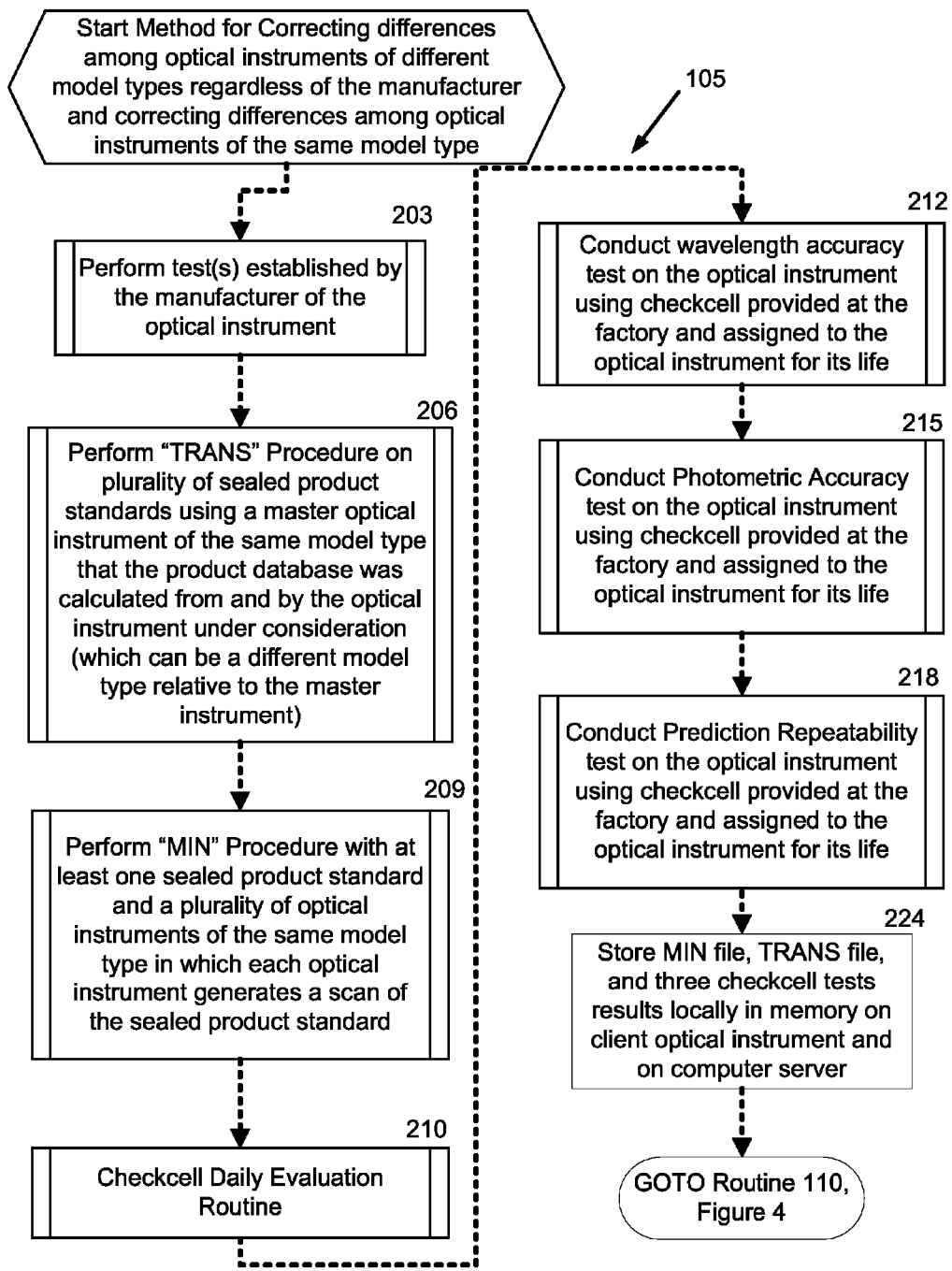
FIG. 2 illustrates the detailed parts of the Routine or Sub-Method for correcting differences among optical instruments of different models regardless of manufacturers and correcting differences among optical instruments of the same model type according to one exemplary embodiment of the invention.

Routine or Sub-Method 105: Correcting Differences Among Optical Instruments 101 of Different Model Types Regardless of Manufacturers and Correcting Differences Among Optical Instruments 101 of the Same Model:

Referring now to FIG. 2, this Figure illustrates the detailed parts of the Routine or Sub-Method 105 for correcting differences among optical instruments 101 of different models regardless of manufacturers and correcting differences among optical instruments 101 of the same model type. The several subroutines illustrated in this Sub-Method are joined by dashed arrowed lines to indicate that the order or sequence of these subroutines could be modified without changing the scope of the invention. The dashed arrowed lines also indicate that processing can stop after any of these subroutines. The dashed arrows also signify that certain routines could be skipped entirely if certain conditions are met.

The Sub-Method 105 can start with a first subroutine 203. The first subroutine 203 can include the performance of tests established by the manufacturer of the optical instrument 101. One of ordinary skill in the art recognizes that most optical instruments 101 are provided with certain diagnostic tests which need to be run and passed before operation of the optical instrument 101.

Next, the second subroutine 206 of the Sub-Method 105 can include performing a "TRANS" procedure which functions to make the optical instrument model being tested to be like ("transforms" the instrument to be like) other optical instruments 101 of a different model. According to this sub-routine 206, the spectra produced by the optical instrument 101 is being examined to determine if the spectra is like the product database 103A, 103B which will be used by the optical instrument 101 to make predictions about products being scanned. The product database 103A, 103B comprises both spectra and reference values from validated methods which correspond to the sample that produced the spectrum.

This routine 206 can be skipped, as authorized by the project manager 109, if it is known that the spectra produced by the optical instrument 101 under evaluation produces spectra like the spectra in the product database 103A, 103B which will be used by the client's optical instrument 101.

The "TRANS" procedure of subroutine 105 can include taking a predetermined number of samples of a product to be analyzed, like wheat, and making sealed standards 107A-C of them. These sealed product standards 107A-C should be impervious to all environmental elements, such as, but not limited to, moisture, ultraviolet radiation, dirt, dust, etc. The predetermined number of sealed product standards 107A-C is generally between about twenty to thirty samples of the product to be analyzed. However, other amounts of sealed product standards 107A-C can be scanned and would be within the scope of the invention.

The physical properties of these sealed product standards 107A-C should remain consistent over time. The same, physical sealed product standards 107A-C should be used by all optical instruments 101 being evaluated.

Once the sealed product standards 107A-C have been established, then the sealed product standards 107A-C should be scanned by a master instrument (which is one of the same optical instrument model that the product database 103A, 103B was calculated from) and by the optical instrument 101 under consideration (which can be a different model relative to the master instrument).

Then, a correction or TRANS file 206' can be generated from these two sets of scans by using anyone of a number of published mathematical procedures known to one of ordinary skill in the art. This correction or TRANS file 206' can be used by the prediction software 160 (PredictStar) operating the optical instrument on a routine basis.

An exemplary mathematical procedure which can be applied to the two sets of scans can include one that makes a shift of all spectra, a slope, and a bias adjustment at each wavelength (Shenk and Westerhaus). Another mathematical procedure includes using single sample standardization by subtraction of the spectra of the same sample scanned by both optical instruments. These two exemplary mathematical procedures are used by FOSS ISS of Denmark.

Another exemplary mathematical procedure includes one which uses piecemeal regression to adjust the wavelengths as they modify the spectrum, using a small section at a time. This mathematical procedure is used by Unity Scientific LLC of Columbia, Md., the assignee at the filing of this writing.

Graph 300A for TRANS Procedure of Subroutine 206:

Referring briefly now to Figure spectrum 3A, this figure illustrates a plot or graph 300A of a spectrum for the same sample but generated by two different optical instrument models. The graph 300A includes an X-axis comprising wavelengths expressed in nanometers and a Y-axis comprising amplitude expressed using the Log 1/R scale. The first spectra 304 or top one in this exemplary embodiment may denote the spectra produced by the master instrument. This first spectrum, 304, could have been produced at the factory which made the master instrument. This first spectrum, 304, could also be an average of several scans made by the master instrument at the factory.

The second spectrum, 302, or lower one in this exemplary embodiment may denote spectrum produced by the model of the optical instrument 101 being evaluated. Assuming these two spectrums graphically represent the differences between these two instrument models, the TRANS file 206' can make it possible for the product database 103A, 103B generated on one instrument model 101 to predict accurately the composition of samples 107D generated on a second instrument or in this case by the client's optical instrument 101. This correction by the TRANS file 206' will generally work for every sample of the product.

In routine operation, the spectrum of a sample 107D is collected by the client optical instrument 101. The sample spectrum is then corrected by the TRANS file 206', and then the processor 121 can use the product (PDA) file 106 to analyze the sample. The PDA file 106 includes, but is not limited to, PLS coefficients to predict the composition, information to calculate a global H (GH) and neighborhood H (NH), as well as other information that may be provided from the spectrum. Further details of the PLS coefficients, NH, and GH values will be discussed below.

MIN Procedure 209 of FIG. 2:

Referring back to FIG. 2, subroutine 209 can include the performance of a "MIN" procedure with at least one sealed product standard and a plurality of optical instruments of the same model in which each optical instrument 101 generates a scan of the sealed product standard 107A-C. If the client optical instrument 101 being evaluated successfully generates a TRANS file 206' in subroutine 206, then this MIN procedure of subroutine 209 may be performed. This MIN procedure generates a MIN file 209' which "minimizes" differences among optical instruments of the same model. If a MIN File 209' has previously been developed for this optical instrument model and product, then this MIN procedure 209 can be skipped entirely.

This MIN procedure 209 is accomplished by scanning at least one sealed product standard 107A-C on about five to ten optical instruments of the same optical instrument model being evaluated. Those scans are provided in a file 209' to the project manager who makes the product (PDA) file 106 (the file used to predict the product composition) for the optical instrument 101. The MIN File 209' produced by this MIN procedure is used in Routine 110 for analyzing new samples 107D. It is retrieved in routine 406 of FIG. 4 by the project manager. The MIN File '209 can be stored on the computer server 117 and retrieved by each client optical instrument 101 and client project manager 109.

The MIN File 209' can be either generated at the factory or by instruments in the field under a common owner. The scans can be collected by an owner of a group of optical instruments 101 or a representative of the product manager. The MIN File 209' is usually only made one time and does not need to be made again for the same product.

Figure 3A:
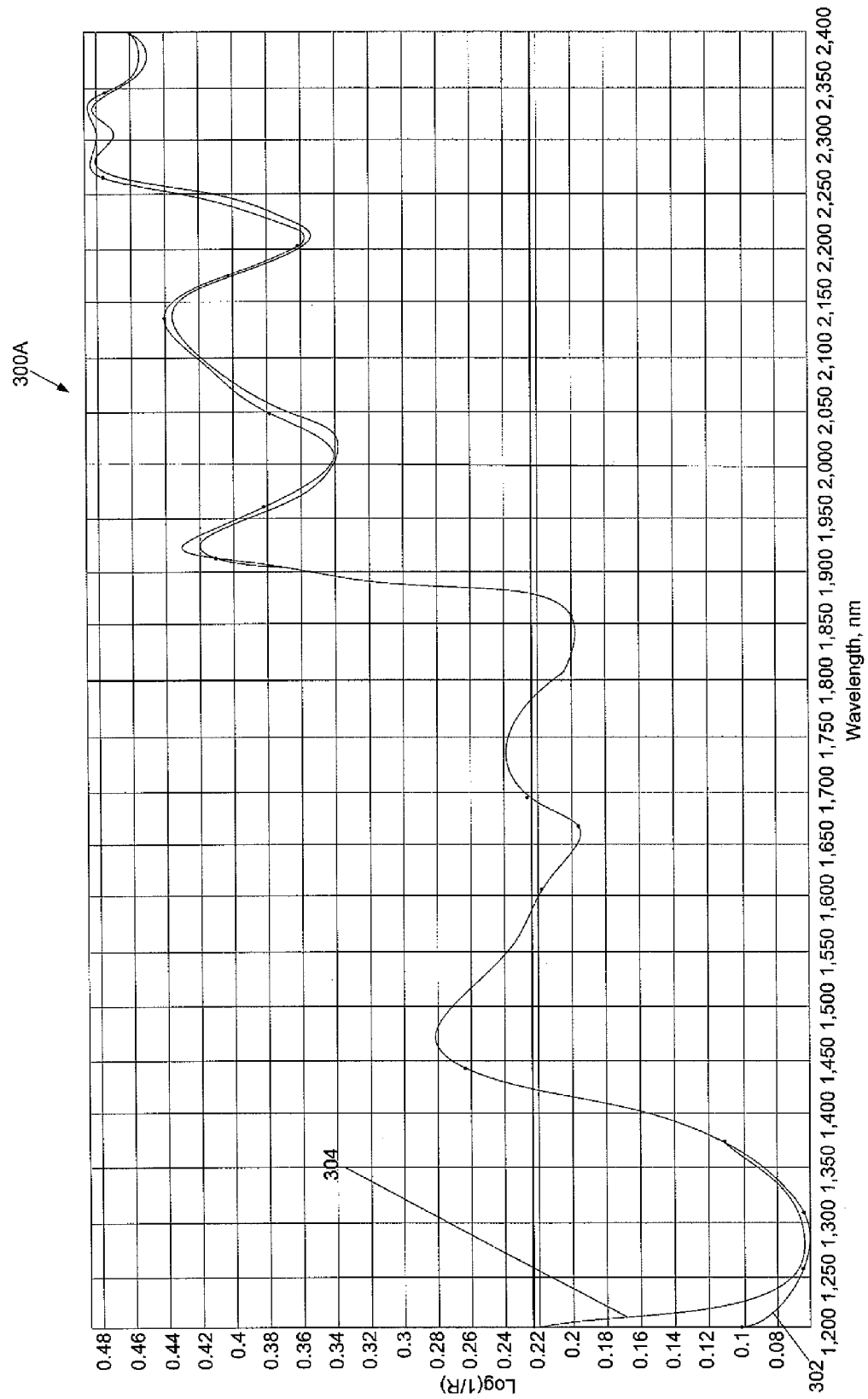
FIG. 3A illustrates a plot or graph of a spectrum for the same sample but generated by two different optical instrument models according to one exemplary embodiment of the invention.
Figure 3B:
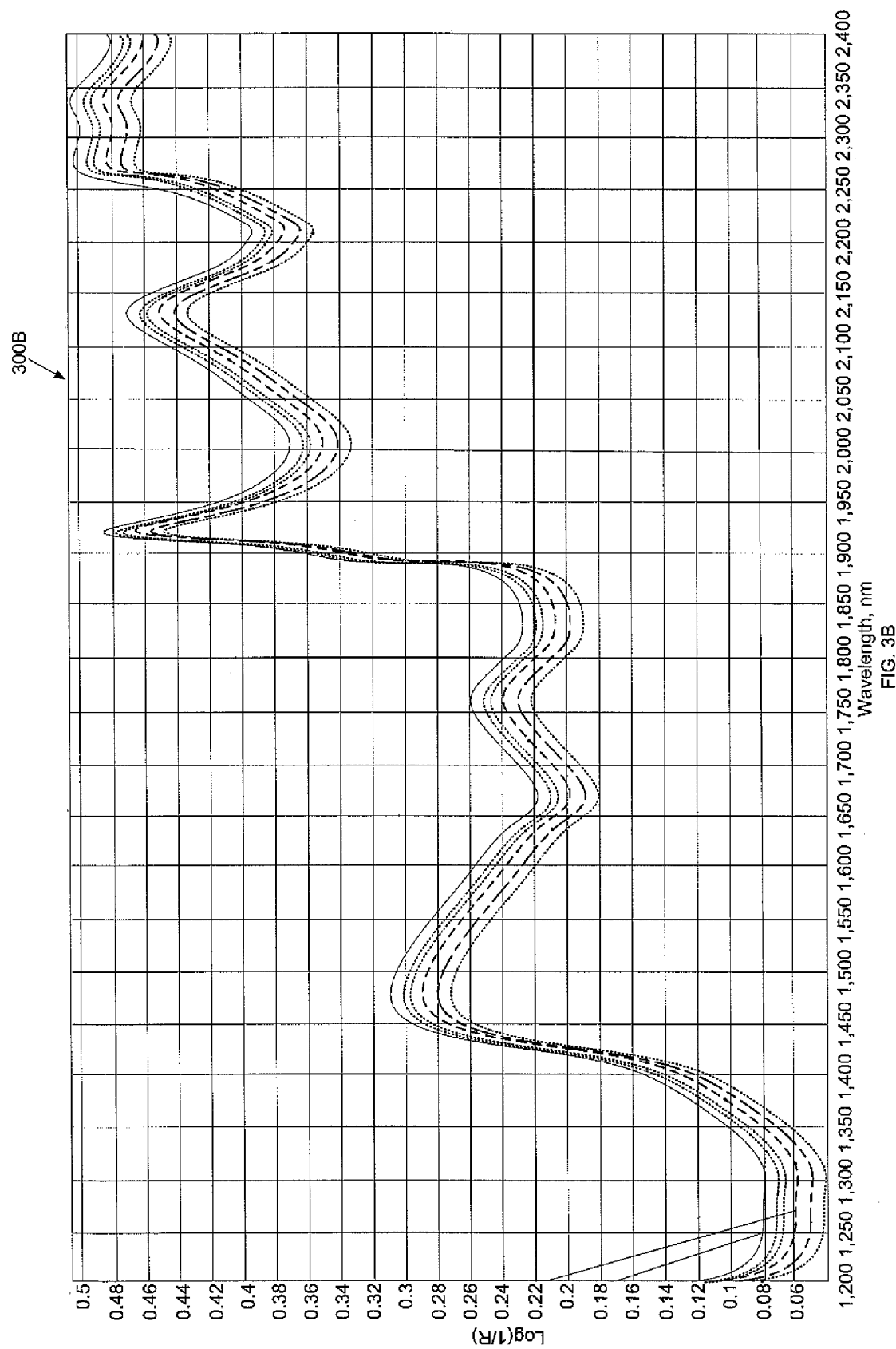
FIG. 3B illustrates a plot or graph of spectra generated by thirty-five optical instruments of the same model measuring the same wheat sample according to one exemplary embodiment of the invention.

Graph 300B for MIN Procedure of Subroutine 209:

Referring briefly now to FIG. 3B, this figure illustrates a plot or graph 300B of spectra generated by thirty-five optical instruments 101 of the same model measuring the same wheat sample. The graph 300B includes an X-axis comprising wavelengths expressed in nanometers and a Y-axis comprising amplitude expressed using the Log 1/R scale. The product can comprise wheat flour. Other products used for the MIN procedure 209 are not beyond the scope of the invention.

This MIN File data shown in FIG. 3B is applied when the wheat product file is being developed. It will usually minimize the differences that exist in predicting the wheat composition among these thirty-five optical instruments and any other instrument of this optical model.

The MIN file 209', is also known as a Repeatability or REP file, and is produced by techniques known to one of ordinary skill in the art, such as those described by the 2007 printed publication entitled, "Handbook of Near-infrared Analysis," authored by Donald A. Burns et al., pp. 370-371, the entire contents of which are hereby incorporated by reference. A MIN or REP file usually contains spectra of one or more sealed standard products scanned under different conditions.

Checkcell Daily Evaluation 210 of Optical Instrument Performance

A checkcell 179, as described previously, is a container that confines a material which has consistent optical properties over the life of an optical instrument 101 and which can determine optical instrument variations over time. According to one exemplary embodiment, the checkcell 179 can comprise a material made from acetyl. However, other materials may be within the scope of the invention. The checkcell 179 used with an optical instrument 101 should be the same one which is used over the life of the optical instrument 101.

The operator of an optical instrument 101 is instructed to scan the checkcell 179 with the prediction program (PredictStar) 160 on a daily basis to assure that the instrument 101 is operating properly. The scan of the checkcell 179 has been biased to predict a value on the optical instrument 101 to be fifty point five.

According to this subroutine 210, the checkcell for the optical instrument 101 under consideration has been scanned at the factory or in the field if necessary and the resulting predicted values produced by a regression equation are biased for a convenience to a mean of fifty point five. A partial least squares (PLS) algorithm is applied to a to an independent file of samples to develop the checkcell product file. This can be performed as known to one of ordinary skill in the art.

With this checkcell product file, each optical instrument will develop a slightly different predicted value because optical instruments 101 are usually never perfectly optically alike. That is why the final predicted value is biased to a mean of fifty point five as noted above. In this way, if multiple optical instruments 101 are being used to scan products, the checkcell 179 for each optical instrument 101 will always produce fifty point five plus or minus a small random error.

The predicted value is plus or minus an error value and that calculated value is tested with a Standard Student T test, known to one of ordinary skill in the art. The result of this two Standard Student T test generates the pass/fail grade for the optical instrument 101, which is reported to the client project manager 109 of FIG. 1B.

The steps for biasing the data to a mean value include, but are not limited to, the following: Scan the checkcell 179 ten times; take the average predicted value and subtract it from fifty point five; add the difference to the equation intercept and the equation to fifty point five. By scanning the checkcell 179 with the checkcell product file on a daily short term basis, the instrument's optical repeatability can be determined.

Another unique feature of the invention is making a more comprehensive evaluation of an optical instrument with automatic routines which can be accessed from the Internet 173. These routines provide long-term evaluation of optical instrument 101.

Checkcell Long Term Certification—Three Tests:

Referring back to FIG. 2, after the Checkcell daily evaluation 210, three tests remain in Routine 105 which include the wavelength accuracy test 212, the photometric accuracy test 215, and the prediction repeatability test 218. These three tests form a checkcell certification. In other words, a single sealed sample (checkcell 179) of a stable material can be used to certify the optical instrument 101 is producing satisfactory spectra over time.

With respect to the MIN and/or TRANS procedures of Subroutines 206 and 209, these two procedures need not be performed for every optical instrument 101 added to the system 104 because these procedures may have been applied on the optical instrument 101 when it was manufactured. If the MIN or TRANS procedures 206, 209 have not been completed by the manufacturer of the optical instrument 101, then they will need to be performed in the field prior to starting the checkcell long term certification noted in this section.

First Internet Checkcell Test: Wavelength Accuracy Test 212 of Optical Instrument 101

In subroutine 212, a wavelength accuracy test, which is the first of the three checkcell tests, is made on the optical instrument 101. The wavelength accuracy test is conducted with the checkcell 179 that is provided by the manufacturer of the optical instrument 101.

According to the wavelength accuracy test, the wavelength peaks of the material forming the checkcell 179 is mathematically compared to known peaks for this material. Usually, less than the entire spectrum of peaks for the known material are compared to the predicted spectrum generated by the optical instrument 101. According to one exemplary embodiment, a predetermined number of peaks are compared to the peaks of the spectrum produced by the optical instrument 101 being evaluated.

This predetermined number of peaks can comprise at least five, but other numbers greater than or less than this amount are within the scope of the invention. Any number of repeatable peaks spaced across the spectrum can be selected for this wavelength accuracy test. A limit in nanometers is determined by the manufacturer as to the range in the discrepancy between the actual and found peaks. This is converted to a pass/fail grade for an optical instrument 101 which is report to the client project manager 109 of FIG. 1B. The optical instrument 101 must pass all wavelengths evaluated to get the pass/fail rating.

Second Internet Checkcell Test: Photometric Accuracy Test 215 of Optical Instrument 101

In subroutine 215, a photometric accuracy test 215 is performed on the optical instrument 101 of interest. This is the second test of the three long term checkcell tests.

The photometric comparison is made to verify that the absorbance of the spectra agrees mathematically with the form and shape of the checkcell material. A mathematical/statistical comparison is made in Log 1/R form and a scattered corrected form. The result of this test yields a pass/fail grade for the optical instrument 101 which is reported to the client project manager 109 of FIG. 1B.

Figure 3C:
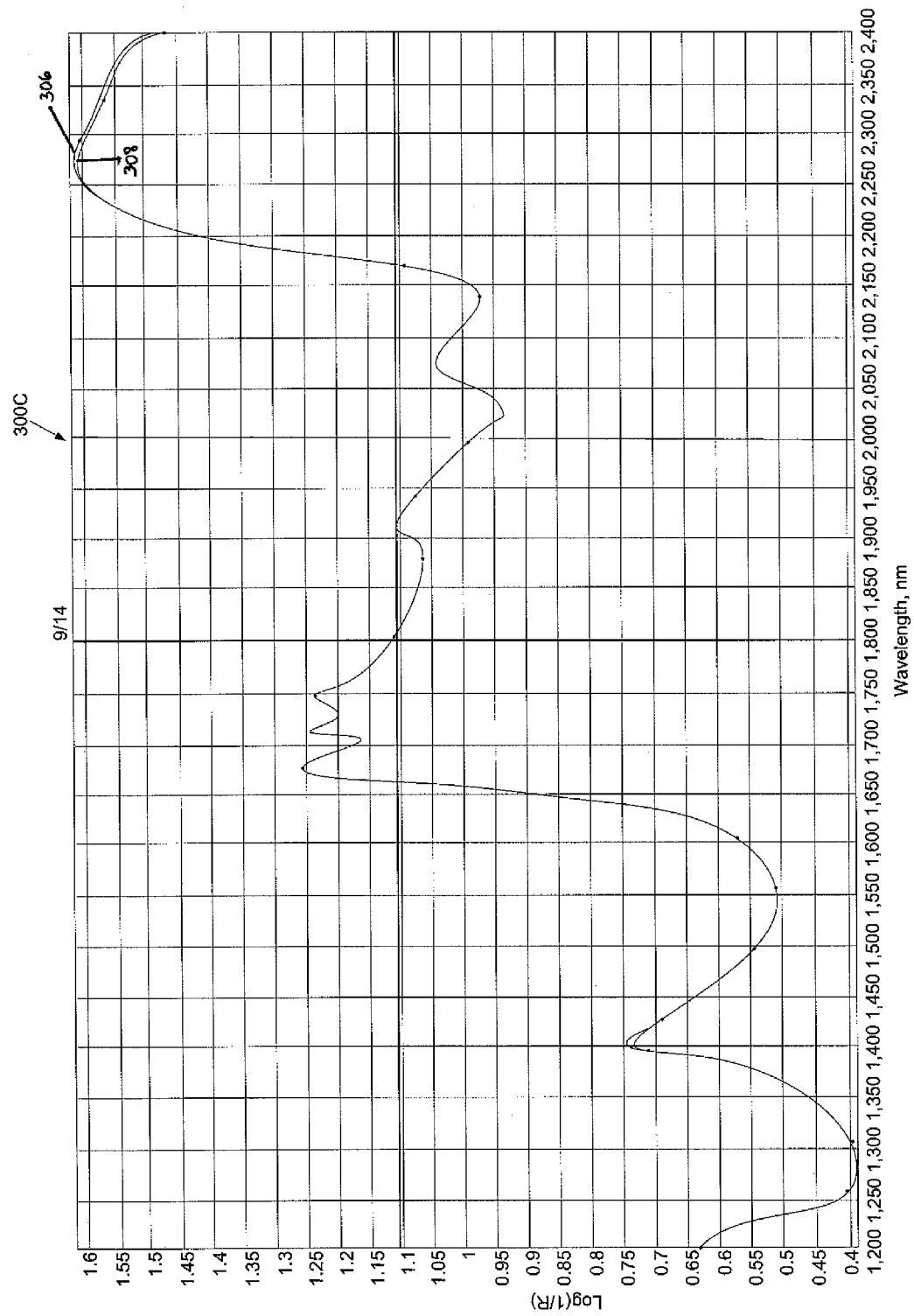
FIG. 3C illustrate plots or graphs of spectra generated by at least two optical instruments of the same model measuring the same checkcell according to one exemplary embodiment of the invention.

Graphs 300C & 300D of FIGS. 3C, 3D—Photometric Accuracy Test 215

Refer briefly now to FIGS. 3C and 3D, these figures illustrate plots or graphs 300C, 300D of spectra generated by at least two optical instruments 101 of the same model measuring the same checkcell 179. The graphs 300C, 300D highlight the differences between a first scan and a current scan of the same checkcell 179. The graphs 300C, 300D can include an X-axis comprising wavelengths expressed in nanometers and a Y-axis comprising amplitude expressed using the Log 1/R scale.

Graph 300D is a mathematically treated version of Graph 300C. In other words, according to one exemplary embodiment, Graph 300D can be formed by taking the derivative of the data expressed in the Graph 300C.

The lighter colored data line 306 compared to the darker colored data line 308 does yield some differences. These differences can be computed by standardization, in which the root mean square is computed across all data points.

A standard Student T test, known to one of ordinary skill in the art, is applied to the two data sets listed in Graphs 300C, 300D. The Student T test can be used to determine whether the means between the two spectra are distinct, provided that the underlying distributions of the spectra are assumed to be normal. If the calculated T value from the Student T test is below the threshold chosen for statistical significance (usually selected at the 0.05 level or 95%), then the null hypothesis which usually states that the two groups do not differ is rejected in favor of an alternative hypothesis, which typically states that the groups do differ. The results of these two Standard Student T tests for the two Graphs 300C, 300D yields a pass/fail grade for the optical instrument which is reported to the client project manager 109 of FIG. 1B.

Third Internet Checkcell Test: Prediction Repeatability Test 218 of Optical Instrument 101

In subroutine 218, a prediction repeatability test 218 is performed on the optical instrument 101 of interest similar to the one used in the short term daily evaluation. This is the third test of the three checkcell tests. The prediction equation is developed by project manager (person operating client project manager 109 of FIG. 1B) for the checkcell 179. The project manager usually makes an equation for each optical instrument type. Each equation can be derived with a simple generic database using a PLS regression technique known to one of ordinary skill in the art. The project manager needs only to create an equation once for all optical instruments 101 of a single optical instrument model.

If the optical instrument 101 passes all three checkcell tests noted above, then a report of the individual checkcell spectra and tests are posted in the client In folder (see FIG. 1C) on the computer server 117 (FIG. 1B) and also sent to the client optical instrument 101.

In Step 224, the MIN File 209', TRANS file 206', and the three checkcell test results can be stored locally in memory on the client optical instrument 101 and archived on the computer server 117. The process then continues to Routine 110 of FIG. 4.

Routine 110—Analyzing New Samples 107D Over Time and Maintaining Accuracy of the Predictions as Compared to a Reference Method Over Time—"Optical Instrument Prediction Accuracy"

Figure 4:
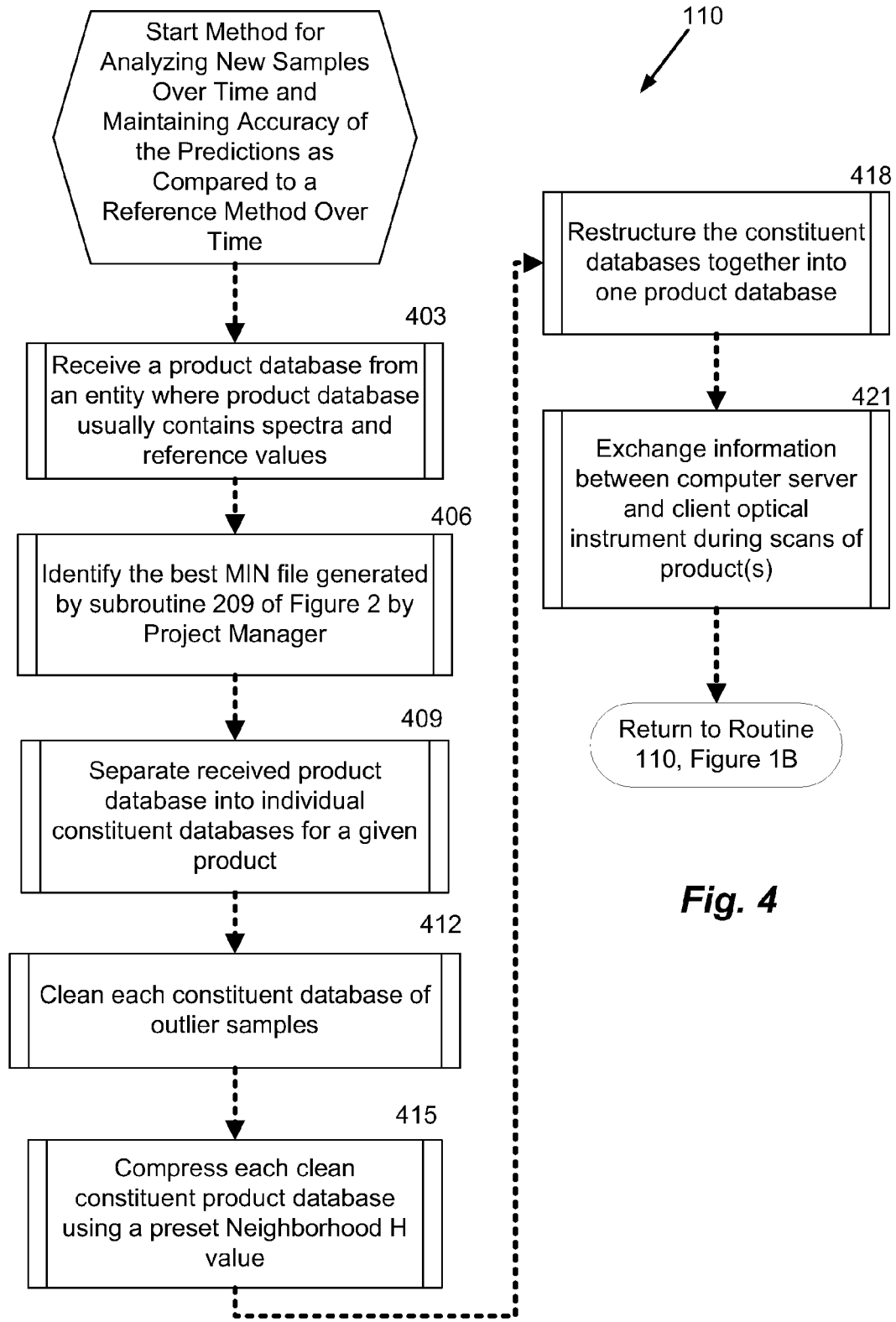
FIG. 4 illustrates the detailed parts of the routine or submethod for analyzing new samples over time and maintaining accuracy of the predictions as compared to a reference method over time according to one exemplary embodiment of the invention.

Referring now to FIG. 4, this Figure illustrates the detailed parts of the Routine or Sub-Method 110 for Analyzing New Samples 107D Over Time and Maintaining Accuracy of the Predictions as Compared to a Reference Method Over Time. The several subroutines illustrated in this Sub-Method are joined by dashed arrowed lines to indicate that the order or sequence of these subroutines could be modified without changing the scope of the invention. The dashed arrowed lines also indicate that processing can stop after any of these subroutines. The dashed arrows also signify that certain routines could be skipped if certain conditions are met.

The first subroutine 403 of the Sub-Method 110 is receiving a product database 103B from an entity, such as a company. A product database 103B usually contains spectra and reference values which are calculated from a validated method. Next, in step 406, a project manager (person operating client project manager computer 109) receives the MIN File 209' generated for this product by subroutine 209 of FIG. 2.

Since there are only a few MIN files 209' for many products, the project manager (person operating client project manager computer 109) needs to find the best file for a given product. This is accomplished by calculating principal component analysis (PCA) files for each MIN File 209' available to the project manager. Next, the product database 103B is reviewed and it is determined which of the MIN files 209' are most like the product database 103B. This is simply done by taking the MIN File 209' of all files available that has the smallest average GH value relative to the product database 103B. A MIN File 209' that is very much like the product database 103B, even though it is not perfectly like the a product to be scanned, is better to reduce the variation among optical instruments 101 of the optical instrument model than no MIN File 209' at all.

The project manager is now ready to begin development of the first prediction file (PDA) 106 for an optical instrument 101. The project manager has the product database 103A and the MIN File 209' to begin the development of the beginning prediction (PDA) file 106 for a client optical instrument 101.

The following four subroutines, 409-418, can be performed automatically by a computer server 117. In subroutine 409, the received product database 103B is separated into individual constituent databases for a given product. For example, if the product database 103B is for wheat, then such a database 103B may include files for various chemical properties of wheat like moisture, protein, and fiber. The database 103B is then separated according to the three chemical properties of moisture, protein, and fiber.

Usually, each file in the product database 103B has an identifier which corresponds to each of the chemical properties. In other words, each file may have an identifier field, like "moisture" to denote moisture, "protein" to denote protein, and "fiber" to denote fiber, etc., etc. The computer server 117 can separate each of the files from one another using the identifier field.

As noted previously, a product database 103B may comprise spectra and reference values. Some spectra in the product database 103B may have reference values, however, some spectra may not have corresponding reference values. The spectra without reference values will not be included in each constituent database that is formed during this separation subroutine 409.

File Cleaning SubRoutine 412

Next, in subroutine 412, each constituent database is cleaned of outlier samples. Neighborhood H (NH), Global H (GH), and the T values are generated by applying Partial Least Squares (PLS) to each constituent database. PLS is known to one of ordinary skill the art. GH values, known to one of ordinary skill in the art, are calculated as the distance from the population average or center. NH values, as known to one of ordinary skill in the art, are the distances between each spectra and it's closest neighbor. T values, as known to one of ordinary skill in the art, are those calculated as the difference between a reference value for the spectra and the PLS predicted value.

Once these parameters are calculated, spectra are removed from the constituent database and the database 103B is considered clean. This action is taken because these outlier spectra and reference values usually add nothing to the database and are best eliminated.

Figure 5A:
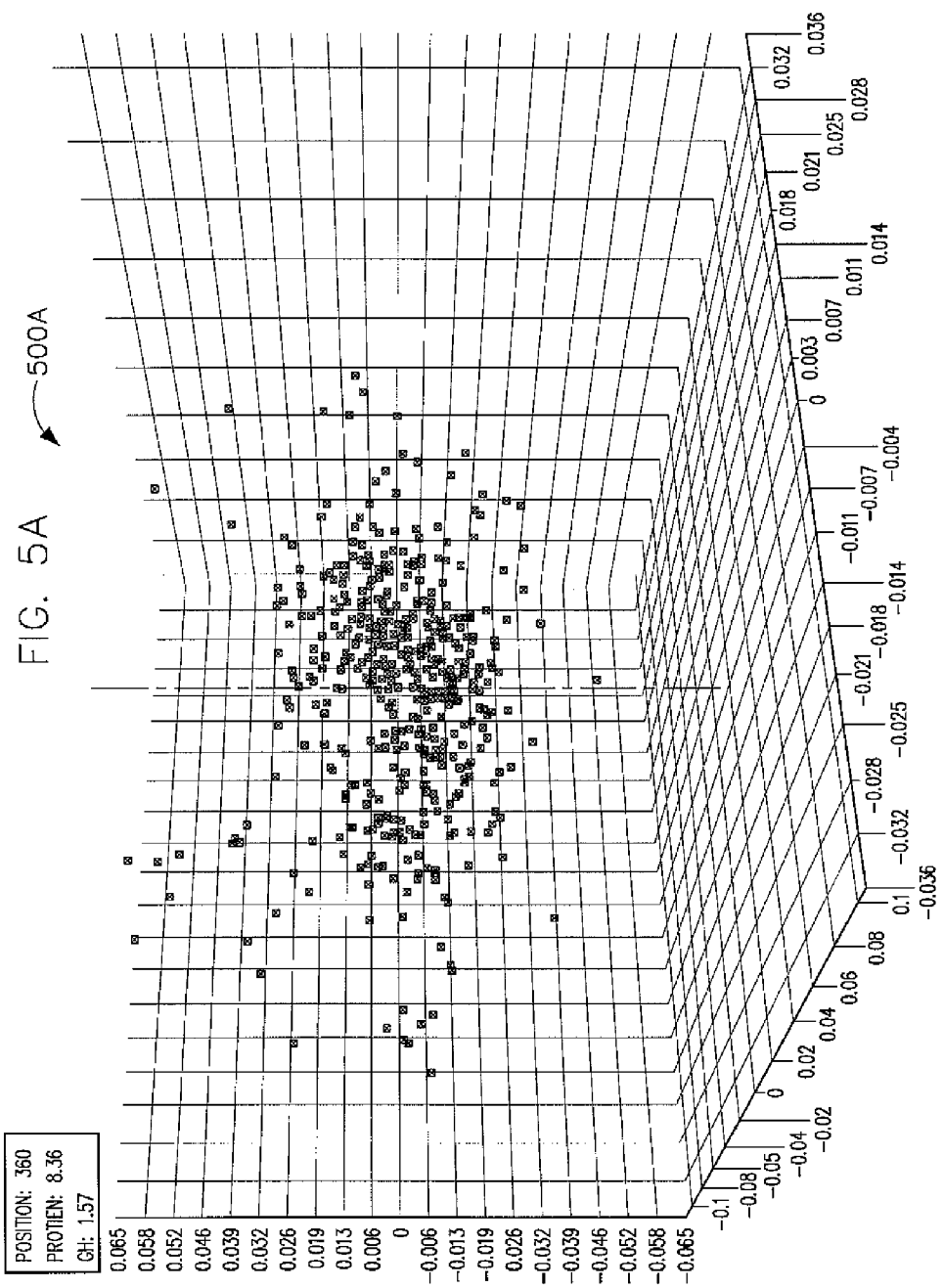
FIG. 5A is a graph of an exemplary product database for flour protein in three dimensions which illustrates the distribution of spectra with a Mahalanobis hyposphere after the product database has been cleaned according to one exemplary embodiment of the invention.

Graph 500A of FIG. 5A—Example of Cleaned Constituent Database:

Referring briefly now to FIG. 5A, this figure is developed in three dimensions to show the distribution of spectra with a Mahalanobis hyposphere. As known to one of ordinary skill in the art, Mahalanobis distance is a distance measure introduced by P. C. Mahalanobis. It is based on correlations between variables by which different patterns can be identified and analyzed. It is a useful way of determining similarity of an unknown sample set to a known one.

A graph 500A is displayed of an exemplary constituent database for flour protein which has been cleaned from 480 samples to 460 samples. The graph 500A is three dimensional and can include an X-axis denoting factor 1, which explains the most variation in the constituent database. The Y-axis denotes a factor 2 which is the second most variation, and the Z-axis denoting factor 3, which contains the third most variation. Other dimensions are present but only three can be displayed at one time.

Condensing or Compressing SubRoutine 415 of FIG. 4

Referring back to FIG. 4, in subroutine 415, each clean constituent product database is now compressed using a preset Neighborhood H value. Neighborhood H values are known to one of ordinary skill in the art. Both spectra and reference values within each constituent product database are averaged within each Neighborhood H distance. It is believed that the steps used in this subroutine 415 are one of the several unique aspects of the invention.

Specifically, assuming each constituent database has been cleaned of T and H outlier samples which is performed in subroutine 412 above, the PLS method is applied to the cleaned data in subroutine 415 and a second PLS regression equation is developed along with new GH and NH values for each constituent database. As noted previously, the PLS method is known to one of ordinary skill in the art.

Next, the average NH is calculated for each constituent database. Then Condensing is performed by changing the size of the average NH value by a constant or percentage (%) (such as by 10, 20, or 30% etc). This then creates a threshold. All of the sample values inside these expanded neighborhoods are then averaged (both spectra and reference values) giving a reduced number of samples in the constituent database. Then the PLS method, which has a regression equation, is applied to the values of the increased neighborhood for calculating new NH and GH values.

Each condensed constituent database is then recalculated with PLS and the last constituent equation is made along with its GH and NH values. This means that three PLS regression equations have been developed for each constituent database: The first is made with all clean samples of each cleaned constituent database; the second with the increases in NH size for each constituent database; and the last (third) after each constituent database is condensed.

The standard error of calibration (SEC) and standard error of cross validation (SECV) of each of these equations for each constituent database are calculated. If the SECV and SEC of the final equation is smaller than the first equation on all clean samples, the condensing has been successful. SEC and SECV are known to one of ordinary skill in the art.

This condensing subroutine 415 can be applied over and over beginning with each constituent clean database and changing the NH percent expansion (%) until the optimum condensing level for each constituent database is found. Even though the coefficients of NH and GH, which are specific to a constituent, are generated independently for each constituent, they are combined into the prediction (PDA) file 106 which is used by each optical instrument when scanning products.

After the optimum condensing level is found for each constituent database, the constituent databases are put back together or restructured in subroutine 418 into one product database with all samples retained from the condensing subroutine 415. This restructured product database 103B is now ready for expansion with new selected samples as will be described below. Next, in subroutine 421, the computer server and client optical instrument can exchange information. Further details of subroutine 421 will be described below in connection with FIG. 6.

Figure 5B:
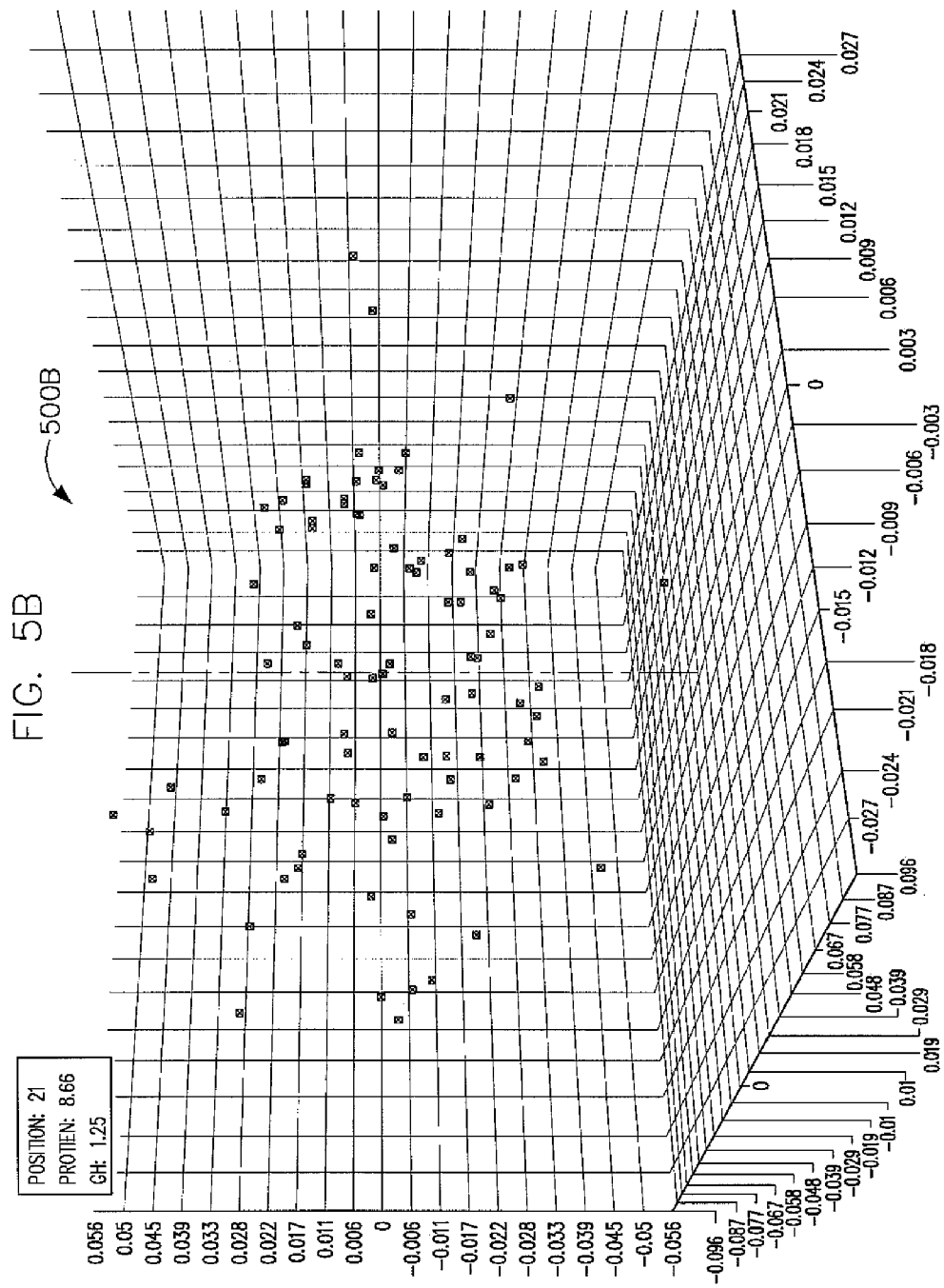
FIG. 5B is a graph of an exemplary product database for flour protein in three dimensions which illustrates the distribution of spectra with a Mahalanobis hyposphere after the product database has been condensed or compressed according to one exemplary embodiment of the invention.

Graph 500B of FIG. 5B—Example of Condensed Constituent Database:

Referring briefly now to FIG. 5B, this figure provides a graph 500B of an exemplary product database for flour protein which has been condensed from the 460 samples of FIG. 5A to 91 samples. The graph 500B is three dimensional as was described above in connection with FIG. 5A. It can be seen that the overall three dimensional space has been maintained but the samples (discrete points) are now more uniformly distributed in the hyperspace. This condensing procedure restructures the constituent database so it is more robust for prediction. New samples added to each constituent database for expansion now have more weight in redirecting the new PLS equation to represent the current samples being analyzed.

Figure 6:
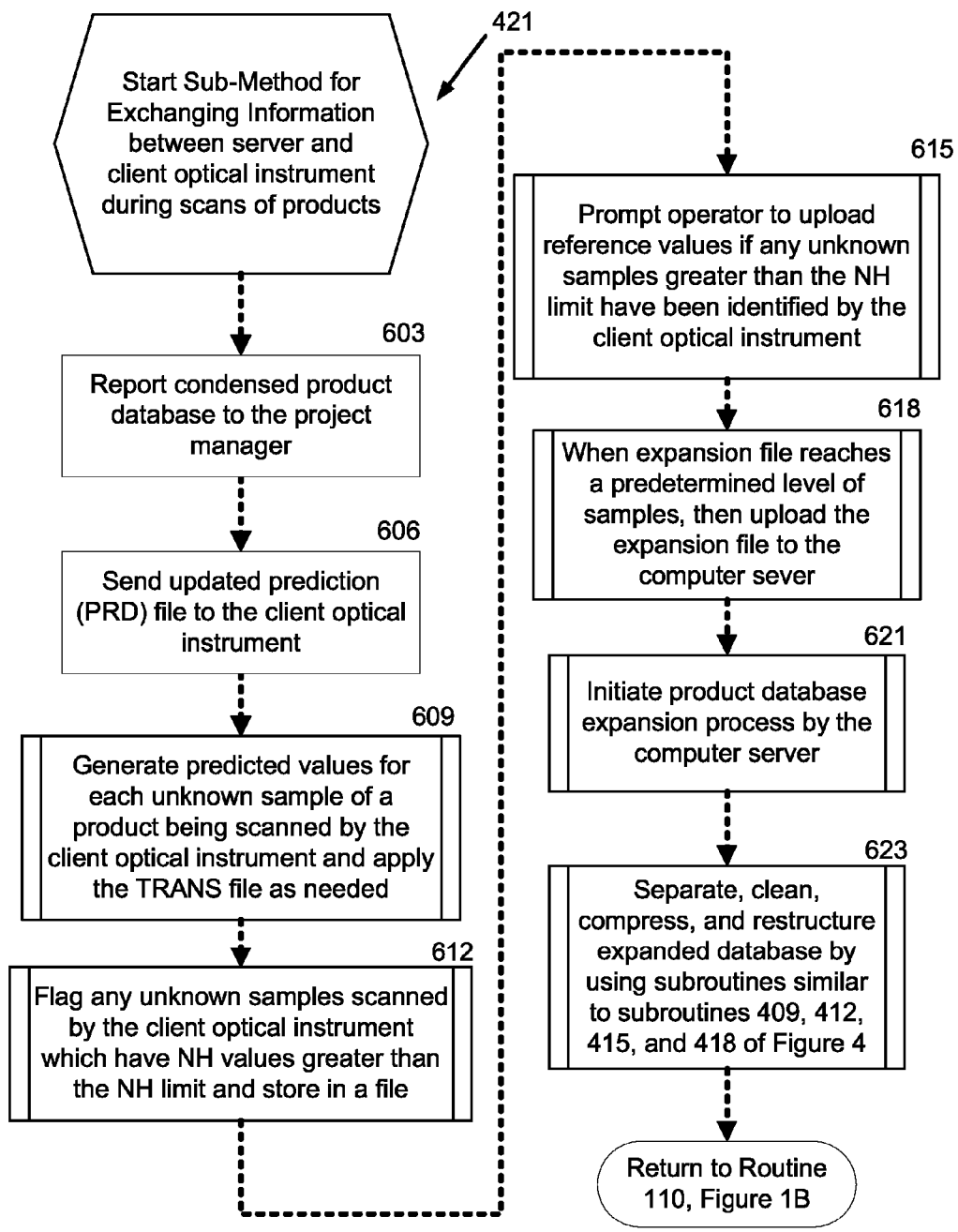
FIG. 6 illustrates the detailed parts of the subroutine of FIG. 4 for the server/client optical instrument information exchange process according to one exemplary embodiment of the invention.

Server/Client (Predictstar) Optical Automatic Product Expansion Subroutine 421 of FIG. 6:

Referring now to FIG. 6, this Figure illustrates the detailed parts of the Subroutine 421 of FIG. 4 for the server/client optical instrument information exchange process. The prediction program 160 (sold under the trade name of "PredictStar" as of this writing) is the optical instrument operation program that can execute this Subroutine 421 as well as processing the scans of the checkcell 179 daily. The prediction program 160 ("Predict Star") can perform sample prediction, and identify the samples to be used to expand the database 103B. Because instrument manufacturers usually have their own routine operation scanning programs 135 for their own instruments, the prediction program 160 can be designed to operate in the background behind the instrument manufacturers routine operation scanning program 135.

When operating in the background, the spectra collected by the instrument manufacturer's routine operation scanning program 135 can be intercepted by the prediction program 160 ("PredictStar") and all of the features described in this disclosure are available to optical instrument running the manufacturer's scanning program 135. This approach in which the prediction program 160 runs in the background relative to a manufacturer's scanning program 135 is very successful and allows this invention to operate independent of instrument platforms.

Step 603 of FIG. 6 is the first step of subroutine 421 in which the condensed product database 103B is reported or sent to the project manager (person operating client optical manager 109 of FIG. 1B). Next, in Step 606, the updated prediction (PDA) file 106 can be sent to the client optical instrument 101. The prediction (PDA) file 106 will usually contain a summary of all variation, PLS coefficients to prediction regression; NH, GH, values, and other information used by an optical instrument 101 on a daily basis to predict unknown samples 107D of a product scanned by the optical instrument 101.

This subroutine 421 provides the client with a completely automatic way of improving the accuracy of the optical instruments accuracy over time without complicated calibration software. This is another one of the primary features of this invention. It operates as follows from the folder structure or hierarchy 102 used by the server 117 illustrated in FIG. 1C.

In subroutine 609, predicted values are generated with the prediction PDA file 106 from the spectra of each unknown sample of a product being scanned by the client optical instrument 101 with the prediction program 160 (Predictstar) on the client's optical instrument 101. Once the spectra of a sample is obtained, the prediction program 160 applies the TRANS file 206' (from routine 206 of FIG. 2) if needed. The TRANS file 206' is applied by the prediction program 160 if such a TRANS file 206' exists. As noted previously, the TRANS file 206' functions to make the optical instrument models that are scanning the current unknown samples 107D to be like ("transforms" the instrument 101 to be like) other optical instruments 101 of a different model.

In subroutine 612, any new samples 107D scanned by the client optical instrument 101 which are not well represented in the client's constituent product database 103B will have NH values greater than the NH limit are flagged and stored in a separate expansion file 188. The operator of the client optical instrument 101 is alerted of these unusual samples 107D having NH values greater than the NH limit stored in the PDA file 106. These new samples 107D having NH values greater than the NH limit will form new samples 107D to expand the product database 1038.

In subroutine 615, those samples 107D selected which are not well represented in the constituent database 103B using the NH values will need reference values from a validated method for that constituent. The operator of the optical instrument 101 will be prompted to add the reference values for the selected samples 107D. As noted previously, reference values are determined using validated methods such as wet chemistry. The operator can insert the reference values in the expansion file 188 which are positioned adjacent to the spectra produced for the unknown sample having NH values greater than the NH limit.

Next, in subroutine 618, when this expansion file 188 containing the new spectra and reference values reaches a predetermined level of samples, which can be thirty as an example, then the prediction program 106 running on the client optical instrument 101 can upload the expansion file 188 with reference values to the computer sever 117.

In subroutine 621, the product database expansion process can be initiated by the computer server 117. During this routine 621, the computer server can retrieve the restructured product database 103B of subroutine 418, the PDA file 106 that goes with each restructured constituent database, and the expansion file 188 uploaded by the client in step 618, and picks up the MIN File 209' from subroutine 209 of FIG. 2 associated with product.

Next, in routine 623, if the database 103B is to be automatically expanded with samples 107D identified as unique in the daily use of this analysis system 104, the expansion and recalibration sequence that follows is very similar to the development of the initial database 103B discussed above in connection with FIG. 4, but the evaluation procedure in this routine 623 has some differences compared to the subroutines of FIG. 4.

The first step of this routine 623 occurs by taking the current PRD prediction file 106 and generating the prediction values for each spectra and constituent in the expansion file 188. These predictions are compared to the actual reference values for the samples provided with the expansion spectra. The standard error of prediction (SEP) is then calculated for each constituent of the expansion files 188 and stored for reference. SEP is known to one of ordinary skill in the art.

The expansion file 188 is then merged with the current product database and cycled through the separation, cleaning, condensing, restructuring of the database 1038 and recalibration, similar to subroutines 409, 412, 415, and 418 discussed above in connection with FIG. 4. After these routines subroutines 409, 412, 415, and 418 are completed, the new expanded PRD prediction file 106 is used to retest the accuracy of the original expansion file 188.

If the SEP of the new expanded product database 103B is less than the original SEP of the expansion file 188, the expansion of the database 103B was successful. If the expanded database SEP value is greater than the original SEP of the stored expansion file 188, the expansion sequence was not successful. This should not happen very often (no more than five times out of one-hundred automatic expansion events), but if it does, a message from the optical instrument 101 is sent to the client project manager 109 who can help determine the cause for the error in the expansion. The expansion of the product database can be performed as often as needed for a given situation. This automated expansion of the database 103B is one of the major breakthroughs of the invention.

Alternative embodiments of the method and system for increasing optical instrument calibration and prediction accuracy within and across different optical instrument platforms become apparent to one of ordinary skill in the art to which the invention pertains without departing from its spirit and scope. Thus, although this invention has been described in exemplary form with a certain degree of particularity, it should be understood that the present disclosure is made only by way of example and that numerous changes in the details of construction and the combination and arrangement of parts or steps may be resorted to without departing from the scope or spirit of the invention. Accordingly, the scope of the present invention may be defined by the appended claims rather than the foregoing description.

What is claimed is:

1. A computer-implemented method for increasing optical instrument calibration and prediction accuracy within and across different optical instrument platforms, comprising:
   generating a MIN file that minimizes differences among optical instruments of a same optical instrument model by scanning one or more sealed product standards with a plurality of optical instruments of a same optical instrument model;
   receiving data conducted from one or more tests with a checkcell;
   creating a prediction file based on the MIN file for an optical instrument; and
   predicting properties of a sample with an optical instrument that applies the prediction file.

2. The computer-implemented method of claim 1, wherein the one or more tests comprise one of a checkcell optical performance test, a wavelength accuracy test, a photometric accuracy test, and a prediction repeatability test.

3. The computer-implemented method of claim 2, wherein the checkcell optical performance test comprises developing a checkcell product file by applying a partial least squares (PLS) algorithm to an independent file comprising several scans of the checkcell.

4. The computer-implemented method of claim 2, wherein the wavelength accuracy test comprises comparing optical wavelength peaks produced by an optical instrument scanning the checkcell against known optical wavelength peaks based on the material used in the checkcell.

5. The computer-implemented method of claim 2, wherein the photometric accuracy test comprises verifying that absorbance of spectra in material contained by the checkcell agrees mathematically with a known form and shape of the material contained by the checkcell.

6. The computer-implemented method of claim 2, wherein the prediction repeatability test comprises developing a prediction equation for the checkcell by using a database and applying a partial least squares regression algorithm to the database.

7. The computer-implemented method of claim 1, further comprising storing the results of the checkcell tests and the MIN file in a location which is assessable by an optical instrument.

8. The computer-implemented method of claim 1, wherein each optical instrument is coupled to a computer communications network.

9. The computer-implemented method of claim 1, further comprising generating a TRANS file by comparing scans of sealed product standards made by a master instrument and an optical instrument under consideration.

10. The computer-implemented method of claim 1, further comprising identifying a sample being scanned by the optical instrument which is outside of a product database based on Neighborhood H values.

11. The computer-implemented method of claim 10, further comprising prompting an operator of the optical instrument to upload reference values for the sample which is outside of the product database.

12. The computer-implemented method of claim 1, wherein generating the MIN file further comprises generating a repeatability file based upon multiple scans of one or more sealed product standards with a plurality of optical instruments of a same optical instrument model.

13. The computer-implemented method of claim 1, wherein conducting one or more checkcell tests with a checkcell comprises conducting one or more checkcell tests with a checkcell comprising acetyl.

14. A computer-implemented method for increasing optical instrument calibration and prediction accuracy within and across different optical instrument platforms, comprising:
   cleaning a product database by removing outlier product samples based on values derived from a regression equation, the product database comprising spectra and reference values; and
   condensing the product database by: calculating averages of values derived from the regression equation applied to the cleaned product database, increasing the averages of the values by a select percentage, and then averaging product samples contained within limits defined by the increased averages of the values.

15. The computer-implemented method of claim 14, further comprising predicting properties of a sample with an optical instrument that compares scans of the sample with the product database.

16. The computer-implemented method of claim 14, further comprising separating the product database into individual constituent databases.

17. The computer-implemented method of claim 14, wherein the regression equation comprises partial least squares.

18. A system for increasing optical instrument calibration and prediction accuracy within and across different optical instrument platforms, comprising:
   a computer communications network;
   a plurality of optical instruments coupled to the computer communications network; and
   a computer server coupled to the computer communications network, the computer server having a processor for executing instructions that make the processor operable for:
      cleaning a product database by removing outlier product samples based on values derived from a regression equation; and
      condensing the product database by: calculating averages of values derived from the regression equation applied to the cleaned product database, increasing the averages of the values by a select percentage, and then averaging product samples contained within limits defined by the increased averages of the values.

19. The system of claim 18, further comprising a project manager client coupled to the computer communications network and being able to access files for each optical instrument managed by the computer server.

20. The system of claim 18, wherein each optical instrument automatically conducts one or more tests with a checkcell, wherein each test comprises one of a checkcell optical performance test, a wavelength accuracy test, a photometric accuracy test, and a prediction repeatability test.

* * * * *